United States Patent
Kawashima et al.

[11] Patent Number: 6,057,447
[45] Date of Patent: May 2, 2000

[54] QUINOLINE SULFIDE DERIVATIVES

[75] Inventors: Seiichiro Kawashima; Sumio Terada; Kenichi Saito; Toshiaki Suzuki; Hiroya Sasahara; Toshihisa Kanda; Tsuneo Inoue, all of Tokyo, Japan

[73] Assignee: Zenyaku Kogyo Kabushiki Kaisha, Tokyo, Japan

[21] Appl. No.: 09/147,605

[22] PCT Filed: Jul. 30, 1997

[86] PCT No.: PCT/JP97/02641

§ 371 Date: Feb. 1, 1999

§ 102(e) Date: Feb. 1, 1999

[87] PCT Pub. No.: WO98/04529

PCT Pub. Date: Feb. 5, 1998

[30] Foreign Application Priority Data

Jul. 30, 1996 [JP] Japan .................................. 8-200466

[51] Int. Cl.[7] .......................... A61K 31/47; C07D 215/16
[52] U.S. Cl. ............................................ 546/153; 514/312
[58] Field of Search ............................. 514/312; 546/153

[56] References Cited

U.S. PATENT DOCUMENTS 5,773,449 6/1998 Konishi et al. ........................ 514/312

OTHER PUBLICATIONS

CA 121:57310, Pluta, 1994.
Chemical Abstracts 121:35356, Coghlan, 1994.
Chemical Abstracts 113:39736, Pluta, 1990.
Chemical Abstracts 112:55907, Coghlan, 989, 1989.
Chemical Abstracts 110:154170, Knoll, 1988.
Chemical Abstracts 62:16017g, Kwart.
Chemical Abstracts 52:11055d, Kwart.
Chemical Abstracts 51:17794b, Kulka.

*Primary Examiner*—D. Margaret Seaman
*Attorney, Agent, or Firm*—Oblon, Spivak, McClelland, Maier & Neustadt, P.C.

[57] ABSTRACT

The present invention is directed to quinoline sulfide derivatives with antibacterial activities selectively against Hp, obtained by reacting quinoline-4(1H)-thione derivatives with halides and represented by the formula I

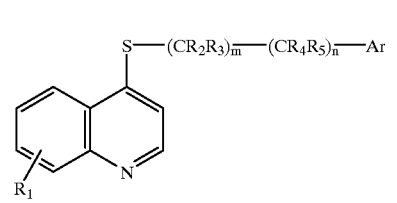

(I)

wherein $R_1$ represents hydrogen or halogen atom, $C_1$–$C_6$ alkoxy, $C_1$–$C_6$ alkylthio or di $C_1$–$C_6$ alkylamino; $R_2$ and $R_3$ respectively represent hydrogen atom or $C_1$–$C_6$ alkyl; one of $R_4$ and $R_5$ represents hydroxyl group and the other represents hydrogen atom or $CR_4R_5$ represents carbonyl; and m and n are integers, m being 1 or 2, n being 0 or 1.

8 Claims, No Drawings

QUINOLINE SULFIDE DERIVATIVES

TECHNICAL FIELD

The present invention relates to novel quinoline sulfide derivatives represented by the formula I and having antibacterial activity against *Helicobacter pylori* or pharmaceutically acceptable salts thereof and antibacterial agents comprising quinoline sulfide derivatives as effective components:

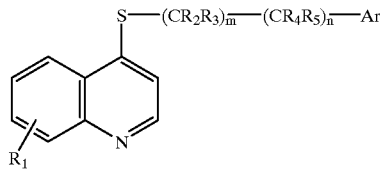

(I)

wherein $R_1$ represents hydrogen or halogen atom, $C_1$–$C_6$ alkoxy, $C_1$–$C_6$ alkylthio or di $C_1$–$C_6$ alkylamino; $R_2$ and $R_3$ respectively represent hydrogen atom or $C_1$–$C_6$ alkyl; one of $R_4$ and $R_5$ represents hydroxyl group and the other represents hydrogen atom or $CR_4R_5$ represents carbonyl; m and n are integers, m being 1 or 2, n being 0 or 1; Ar represents, in a case where n is 0, a group of the formula II or III

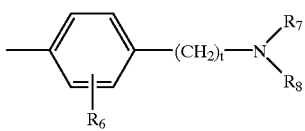

(II)

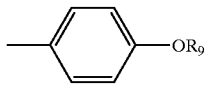

(III)

wherein $R_6$ represents hydrogen atom, $C_1$–$C_6$ alkyl or di $C_1$–$C_6$ alkylamino; $R_7$ represents hydrogen atom, $C_1$–$C_9$ alkyl, hydroxy $C_1$–$C_6$ alkyl, napthoyl $C_1$–$C_6$ alkyl, acetoxy $C_1$–$C_6$ alkyl, $C_1$–$C_6$ alkoxycarbonyl, trihalo $C_1$–$C_6$ alkoxycarbonyl, di $C_1$–$C_6$ alkylaminoacetyl or di $C_1$–$C_6$ alkylamino $C_1$–$C_6$ alkyl; $R_8$ represents hydrogen atom, $C_1$–$C_6$ alkyl, hydroxy $C_1$–$C_6$ alkyl or acetoxy $C_1$–$C_6$ alkyl, or $NR_7R_8$ represents pyrrolidinyl, piperidino, morpholino or piperazinyl (which may be substituted by $C_1$–$C_6$ alkyl or formyl); $R_9$ represents benzyl; and t is an integer and is 0 or 1;

Ar represents, in a case where n is 1, naphthyl, fluorenyl or a group of the formula IV, V or VI

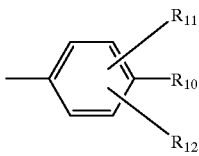

(IV)

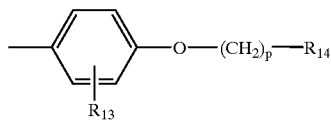

(V)

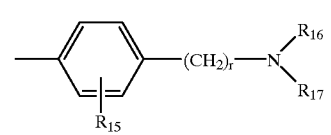

(VI)

wherein $R_{10}$ represents hydrogen atom, $C_1$–$C_6$ alkyl, hydroxyl group, $C_1$–$C_6$ alkoxy, epoxy $C_1$–$C_6$ alkoxy, mono- or dihydroxy $C_1$–$C_6$ alkoxy, phenyl, piperidinyl (which may be substituted by $C_1$–$C_6$ alkylcarbonyl or $C_1$–$C_6$ alkoxycarbonyl), or tetrahydropyridyl (which may be substituted by $C_1$–$C_6$ alkylcarbonyl); $R_{11}$ represents hydrogen atom, $C_1$–$C_6$ alkoxy or benzyloxy; $R_{12}$ represents hydrogen atom or $C_1$–$C_6$ alkoxy; $R_{13}$ represents hydrogen atom or $C_1$–$C_6$ alkoxy; $R_{14}$ represents $C_1$–$C_6$ alkoxycarbonyl, phenyl (which may be substituted by $C_1$–$C_6$ alkoxy), or benzoyl (which may be substituted by $C_1$–$C_6$ alkyl); $R_{15}$ represents hydrogen or halogen atom; $R_{16}$ represents hydrogen atom, $C_1$–$C_6$ alkyl, $C_1$–$C_6$ alkylcarbonyl, $C_1$–$C_6$ alkoxycarbonyl or pyrrolidinyl (which may be substituted by $C_1$–$C_6$ alkoxycarbonyl); $R_{17}$ represents hydrogen atom, $C_1$–$C_9$ alkyl or benzyl, or $NR_{16}R_{17}$ represents piperidino, morpholino, piperazinyl (which may be substituted by $C_1$–$C_6$ alkyl, $C_1$–$C_6$ alkylcarbonyl, $C_1$–$C_6$ alkoxycarbonyl, trihalo $C_1$–$C_6$ alkoxycarbonyl, $C_2$–$C_6$ alkenyloxycarbonyl, phenoxycarbonyl, benzyloxycarbonyl, amino $C_1$–$C_6$ alkylcarbonyl (amino group may be substituted by $C_1$–$C_6$ alkoxycarbonyl), cinnamoyl (which may be substituted by $C_1$–$C_6$ alkoxy), $C_1$–$C_6$ alkylcarbamoyl, di $C_1$–$C_6$ alkylsulfamoyl, $C_1$–$C_6$ alkylsulfonyl, di $C_1$–$C_6$ alkylaminothiocarbonyl, pyrimidyl or phenyl (which may be substituted by halogen atom)), imidazolidinyl (which may be substituted by oxo or $C_1$–$C_6$ alkyl) or homopiperazinyl (which may be substituted by $C_1$–$C_6$ alkoxycarbonyl); p is an integer within a range of 0–5 and r is an integer within a range of 0–2; there is no case where all of $R_1$, $R_2$, $R_3$, $R_{10}$, $R_{11}$ and $R_{12}$ are hydrogen atoms when m and n are respectively 1, $CR_4R_5$ is carbonyl and Ar is the group of the formula IV; $R_1$ is not hydrogen or halogen atom nor $C_1$–$C_6$ alkoxy when m is 1, n is 0 and Ar is 4-aminophenyl.

BACKGROUND ART

*Helicobacter pylori* is a spiral, short rod-shaped, gram-negative bacterium having monopolar and several sheathed flagella. The bacteria are detected both in the gastric mucous layer and on the surface of gastric epithelial cells.

The fact that spiral bacteria live on and in a gastric mucosa has been observed by many researchers. Firstly in 1983, Marshall et al. succeeded in cultivating spiral bacteria through isolation of the same from a gastric mucosa. The bacterium was originally named *Campylobacter pylori* since its shapes and biochemical characteristics are analogous to those of the genus Campylobacter which is one of known enteritis-causing bacterial genera. However, later bacterial taxonomic researches established a new independent genus including the bacterium, and the bacterium was renamed *Helicobacter pylori*. In 1984, Marshall et al. detected the bacteria at high percentage from patients suffering from peptic ulcer such as gastric and duodenal ulcers and chronic gastritis, and suggested relevance of the bacteria to occurrence and recurrence of these diseases. As conventional remedies against peptic ulcer, medical treatments with gastric secretion inhibitors have been utilized; advent of $H_2$-blocker such as cimetidine and proton-pump inhibitor such as omeprazole enhanced the cure rate up to 80–90%. However, it has been reported that about 50% of patients healed with administration of anti-ulcer agents have relapse or recurrence of ulcers within twelve months and that, particularly, patients healed with gastric secretion inhibitors such as $H_2$-blockers and proton-pump inhibitors have relapse rate of as high as 70–90%. Thus, prevention of the relapse or recurrence is one of greatest problems in the treatment.

There have, however, been recently increasingly reported that removal of *Helicobacter pylon* (hereinafter referred to as Hp) with an antibacterial agent will decrease ulcer relapse rate [see for example SAISHIN-IGAKU: Vol. 44, No. 2, pp. 295–302, (1989)]; and, in February 1994, NIH in U. S. A. advised necessity of eradicating Hp in the treatment of peptic ulcer. Hp-eradication agents used nowadays are for example antibiotics and bismuth preparations. Antibiotics are not suitable for long-term use since they may also affect other intestinal bacteria and may cause advent of resistant bacteria. Treatment with bismuth preparations is rather problematic since the bismuth preparations are weak in antibacterial activity and may cause vomiting, diarrhea and/or side effects on central nervous system.

Anti-ulcer agents with antibacterial activities against Hp have been proposed for example in Japanese Patent Provisional Publication (Kokai) Nos. 4-364160 and 5-117268; however, none of the proposed agents have sufficient selectivity and antibacterial activity. Under such circumstances, there have been demand on development of preparations having higher selectivity on Hp as well as having higher antibacterial activity against Hp in the treatment of peptic ulcer and chronic gastritis with Hp infection.

Recently, quinoline-4(1H)-thione derivatives were found to have antibacterial activity selectively against Hp and have been suggested as antibacterial agents against Hp (WO 96/11187). However, there has been still room for inprovement in strength of antibacterial activity.

In order to overcome the above-mentioned problems, we, the inventors carried out intensive studies to find that quinoline sulfide derivatives of the above-mentioned formula I which are obtained by modifying thione functional group of quinoline-4(1H)-thione derivatives have antibacterial activity selectively against Hp and superior to that of the above-mentioned quinoline-4(1H)-thione derivatives, thus accomplishing the present invention.

Known quinoline sulfide derivatives similar to the compounds of the present invention are benzyl sulfide derivatives of quinoline disclosed in Japanese Patent Provisional publication (Kokai) No. 1-246264 and U.S. Pat. No. 5,296,484; disclosed in them is bactericidal effect against botanically pathogenic bacteria or acari- or insecticidal effect. Analogical derivatives are also disclosed in Synthesis (1): 56 (1995). However, no reports have been made on antibacterial effect of these quinoline sulfide derivatives against Hp at all. Provision of quinoline sulfide derivatives as antibacterial agent against Hp is originally proposed in the present application.

DISCLOSURE OF THE INVENTION

The terms used for definition of letters in the formula I by which the compounds of the present invention are represented are defined and exemplified in the following.

The wording "$C_1$–$C_6$" refers to a group having 1 to 6 carbon atoms.

The wording "$C_1$–$C_9$" refers to a group having 1 to 9 carbon atoms.

The "$C_1$–$C_6$ alkyl" refers to a straight- or branched-chain alkyl group such as methyl, ethyl, n-propyl, isopropyl, n-butyl, tert-butyl, n-pentyl, n-hexyl or the like.

The "$C_1$–$C_9$ alkyl" refers to a straight- or branched-chain alkyl group such as heptyl, octyl, nonyl or the like in addition to the groups referred to in the above with reference to "$C_1$–$C_6$ alkyl".

The "$C_1$–$C_6$ alkoxy" refers to a straight- or branched-chain alkoxy group such as methoxy, ethoxy, n-propoxy, isopropoxy, n-butoxy, tert-butoxy, n-pentyloxy, n-hexyloxy or the like.

The "$C_2$–$C_6$ alkenyl" refers to a straight- or branched-chain alkenyl group such as vinyl, propenyl, isopropenyl, butenyl, pentenyl, hexenyl or the like.

The "halogen atom" may be fluorine, chlorine, bromine or iodine atom.

The compounds according to the present invention may be as follows, though the present invention is not limited to these compounds.

4-[2-(4-tert-Butylphenyl)-2-oxoethylthio]quinoline

4-[2-(4-Hydroxyphenyl)-2-oxoethylthio]quinoline

4-[1,1-Dimethyl-2-(4-methoxyphenyl)-2-oxoethylthio]-quinoline

4-[2-(4-Benzyloxyphenyl)-2-oxoethylthio]-7-methoxyquinoline

4-[2-(4-Benzyloxyphenyl)-2-oxoethylthio]quinoline

4-[2-[4-(4-Methoxybenzyloxy)phenyl]-2-oxoethylthio]-quinoline

4-[2-(3-Benzyloxyphenyl)-2-oxoethylthio]quinoline

4-[2-[4-[2-(4-tert-Butylphenyl)-2-oxoethoxy]phenyl]-2-oxoethylthio]quinoline

4-[2-(4-Phenoxyphenyl)-2-oxoethylthio]quinoline

4-[2-[4-(4-Methoxyphenoxy)phenyl]-2-oxoethylthio]quinoline

4-[2-(4-Hydroxy-2-methoxyphenyl)-2-oxoethylthio]quinoline

4-[2-(2,4-Dimethoxyphenyl)-2-oxoethylthio]quinoline

4-[2-[2-Methoxy-4-(4-methoxybenzyloxy)phenyl]-2-oxoethylthio]quinoline

4-[2-[3-Methoxy-4-(4-methoxybenzyloxy)phenyl]-2-oxoethylthio]quinoline

4-[2-[3-Methoxy-4-(2,3-epoxypropoxy)phenyl]-2-oxoethylthio]quinoline

4-[2-[3-Methoxy-4-(2,3-dihydroxypropoxy)phenyl]-2-oxoethylthio]quinoline

4-[2-(2-Methoxy-4-hexyloxyphenyl)-2-oxoethylthio]-quinoline

4-[2-[4-(5-Ethoxycarbonyl-n-pentyloxy)phenyl]-2-oxoethylthio]quinoline

4-[2-(2,3,4-Trimethoxyphenyl)-2-oxoethylthio]quinoline

4-[2-(3,4,5-Trimethoxyphenyl)-2-oxoethylthio]quinoline

4-[2-(4-tert-Butoxycarbonylaminophenyl)-2-oxoethylthio]quinoline

4-[2-(4-Pivaloylaminophenyl)-2-oxoethylthio]quinoline

4-[2-[4-(N-Acetylbenzylamino)phenyl]-2-oxoethylthio]quinoline

4-[2-(4-Benzylaminophenyl)-2-oxoethylthio]quinoline

4-[2-(4-Benzylamino-3-bromophenyl)-2-oxoethylthio]-quinoline
4-[2-(4-Dimethylaminophenyl)-2-oxoethylthio]quinoline
4-[2-[3-Bromo-4-(1-tert-butoxycarbonyl-3-pyrrolidinylamino)phenyl]-2-oxoethylthio]quinoline
4-[2-[4-(3-Isobutyl-5-oxo-1-imidazolidinyl)phenyl]-2-oxoethylthio]quinoline
4-[2-(4-Piperidinophenyl)-2-oxoethylthio]quinoline
4-[2-(4-Morpholinophenyl)-2-oxoethylthio]quinoline
4-[2-(3-Bromo-4-morpholinophenyl)-2-oxoethylthio]-quinoline
4-[2-[4-(4-tert-Butoxycarbonyl-1-piperazinyl)phenyl]-2-oxoethylthio]quinoline
4-[2-[4-[2-(4-tert-Butoxycarbonyl-1-piperazinyl)ethyl]-phenyl]-2-oxoethylthio]quinoline
4-[2-[4-(4-Acetyl-1-piperazinyl)phenyl]-2-oxoethylthio]-quinoline
4-[2-[3-Bromo-4-(4-tert-butoxycarbonyl-1-piperazinyl)-phenyl]-2-oxoethylthio]quinoline
4-[2-[4-(4-Pivaloyl-1-piperazinyl)phenyl]-2-oxoethylthio]quinoline
4-[2-[4-[4-(4-Methoxycinnamoyl)-1-piperazinyl]phenyl]-2-oxoethylthio]quinoline
4-[2-[4-(4-Diethylaminothiocarbonyl-1-piperazinyl)-phenyl]-2-oxoethylthio]quinoline
4-[2-[4-(4-Methyl-1-piperazinyl)phenyl]-2-oxoethylthio]-quinoline
4-[2-[4-(4-Isobutyl-1-piperazinyl)phenyl]-2-oxoethylthio]quinoline
4-[2-[3-Bromo-4-(4-neopentyl-1-piperazinyl)phenyl]-2-oxoethylthio]quinoline
4-[2-[4-[4-(4-Bromophenyl)-1-piperazinyl]phenyl]-2-oxoethylthio]quinoline
4-[2-[4-[4-(2-Pyrimidyl)-1-piperazinyl]phenyl]-2-oxoethylthio]quinoline
4-[2-[4-(4-tert-Butoxycarbonyl-1-piperazinyl)phenyl]-2-oxoethylthio]-6-fluoroquinoline
4-[2-[4-(4-Benzyloxycarbonyl-1-piperazinyl)phenyl]-2-oxoethylthio]quinoline
4-[2-[4-(4-Vinyloxycarbonyl-1-piperazinyl)phenyl]-2-oxoethylthio]quinoline
4-[2-[4-[4-(N-tert-Butoxycarbonylvalyl)-1-piperazinyl]-phenyl]-2-oxoethylthio]quinoline
4-[2-[4-(4-Phenoxycarbonyl-1-piperazinyl)phenyl]-2-oxoethylthio]quinoline
4-[2-[4-[4-(2,2,2-Trichloroethoxycarbonyl)-1-piperazinyl]phenyl]-2-oxoethylthio]quinoline
4-[2-[4-(4-Isobutoxycarbonyl-1-piperazinyl)phenyl]-2-oxoethylthio]quinoline
4-[2-[4-(4-Ethoxycarbonyl-1-piperazinyl)phenyl]-2-oxoethylthio]quinoline
4-[2-[4-(4-Allyloxycarbonyl-1-piperazinyl)phenyl]-2-oxoethylthio]quinoline
4-[2-[4-(4-Methoxycarbonyl-1-piperazinyl)phenyl]-2-oxoethylthio]quinoline
4-[2-[4-(4-Dimethylsulfamoyl-1-piperazinyl)phenyl]-2-oxoethylthio]quinoline
4-[2-[4-[4-(N-tert-Butylcarbamoyl)-1-piperazinyl]phenyl]-2-oxoethylthio]quinoline
4-[2-[4-(4-Methanesulfonyl-1-piperazinyl)phenyl]-2-oxoethylthio]quinoline
4-[2-[4-(4-tert-Butoxycarbonyl-1-piperazinyl)phenyl]-2-hydroxyethylthio]quinoline
4-[2-[4-(1-Piperazinyl)phenyl]-2-oxoethylthio]quinoline hydrochloride
4-[2-(p-Biphenyl)-2-oxoethylthio]-7-methoxyquinoline
4-[2-(p-Biphenyl)-2-oxoethylthio]quinoline
4-[2-(2-Naphtyl)-2-oxoethylthio]quinoline
4-[2-(2-Naphtyl)-2-oxoethylthio]-7-methylthioquinoline
4-[2-(2-Naphtyl)-2-hydroxyethylthio]quinoline
4-[2-(1-Naphtyl)-2-oxoethylthio]quinoline
4-[2-(2-Fluorenyl)-2-oxoethylthio]-7-methoxyquinoline
4-[2-[4-(1-Pivaloyl-4-piperidinyl)phenyl]-2-oxoethylthio]quinoline
4-[2-[4-(4-tert-Butoxycarbonyl-1-homopiperazinyl)phenyl]-2-oxoethylthio]quinoline
4-[3-(4-Methoxyphenyl)-3-oxopropylthio]quinoline
4-[3-(4-Acetoaminophenyl)-3-oxopropylthio]quinoline
4-[2-[4-(Heptylamino)phenyl]-2-oxoethylthio]quinoline
4-[2-[4-(Butylamino)-3-bromophenyl]-2-oxoethylthio]-quinoline
4-[2-(4-(Diethylamino)phenyl]-2-oxoethylthio]quinoline
4-[2-(4-Isopropylphenyl)-2-oxoethylthio]quinoline
4-[2-[4-(1-Pivaloyl-1,2,5,6-tetrahydropyrid-4-yl)-phenyl]-2-oxoethylthio]quinoline
4-[2-[4-(1-tert-Butoxycarbonyl-4-piperidinyl)phenyl]-2-oxoethylthio]quinoline
4-(4-Aminobenzylthio)-7-methylthioquinoline
4-(4-Ethylaminobenzylthio)-7-methythioquinoline
4-(4-Isobutylaminobenzylthio)-7-methoxyquinoline
4-[4-(4-Hydroxybutylamino)benzylthio]-7-methylthioquinoline
4-[4-(3,5,5-Trimethylhexylamino)benzylthiol-7-methylthioquinoline
4-[1-[4-(2,2,2-Trichloroethoxy)carbonylaminophenyl]-ethylthio]-7-methylthioquinoline
4-[4-(2-β-Naphtyl-2-oxoethylamino)benzylthio]-7-methylthioquinoline
4-(3-Methyl-4-methylaminobenzylthio)-7-methylthioquinoline
4-(3-Methyl-4-dimethylaminobenzylthio)-7-methylthioquinoline
4-[3,4-Bis(dimethylamino)benzylthio]-7-methylthioquinoline
4-(4-Dimethylaminobenzylthio)quinoline
4-(4-Dimethylaminobenzylthio)-7-methylthioquinoline
4-(4-Dimethylaminobenzylthio)-7-isopropylthioquinoline
4-(4-Dimethylaminobenzylthio)-7-dimethylaminoquinoline
4-[1-(4-Dimethylaminophenyl)ethylthio]-7-methylthioquinoline
4-(4-Diethylaminobenzylthio)-7-methylthioquinoline
4-[4-(1-Pyrrolidinyl)benzylthio]-7-methylthioquinoline
4-(4-Morpholinobenzylthio)-7-methylthioquinoline
4-(4-Piperidinobenzylthio)-7-methylthioquinoline
4-[4-(4-Methyl-1-piperazinyl)benzylthio]-7-methylthioquinoline
4-[4-(4-Neopentyl-1-piperazinyl)benzylthio]-7-methylthioquinoline
4-[4-(4-Formyl-1-piperazinyl)benzylthio]-7-methylthioquinoline 4-[4-(4-Formyl-1-piperazinylmethyl)benzylthio]
quinoline 4-[4-(4-Formyl-1-piperazinylmethyl)benzylthio]-7-
methylthioquinoline 4-[4-[Bis(2-acetoxyethyl)amino]benzylthio]-7-
methylthioquinoline 4-[4-[N-(2-Acetoxyethyl)-2-hydroxyethylamino]
benzylthio]-7-methylthioquinoline 4-[4-[Bis(2-hydroxyethyl)amino]benzylthio]-7-
methylthioquinoline 4-[2-(4-tert-Butoxycarbonylaminophenyl)ethylthio]-
quinoline 4-[2-(4-Aminophenyl)ethylthio]-7-methoxyquinoline 4-[2-(4-Benzyloxyphenyl)ethylthio]quinoline 4-[2-(4-Dimethylaminophenyl)ethylthio]quinoline 4-[2-[4-[2-(N-Isobutyl-N-methylamino)acetylamino]
phenyl]-ethylthio]quinoline 4-[2-[4-(3-Isobutyl-5-oxo-1-imidazolidinyl)phenyl]
ethylthio]quinoline 4-[2-[4-[N-[2-(N-Isobutyl-N-methylamino)ethyl]-N-
methylamino]phenyl]ethylthio]quinoline The compounds of the present invention may have asymmetric carbon atoms in their structures. It is to be understood that isomers due to such asymmetric carbon atoms or combination (racemic form) of any of the isomers are included in the category of the compounds of the present invention.

Furthermore, the compounds of the present invention may be in the form of pharmaceutically acceptable salts such as acid added salt, alkali salts or organic ammonium salts. The appropriate acid added salts which can be used include, for example, inorganic acid salts such as hydrochloride, sulfate, hydrobromide, nitrate and phosphate, organic acid salts such as acetate, oxalate, propionate, glycolate, lactate, pyruvate, malonate, succinate, maleate, fumarate, malate, tartrate, citrate, benzoate, cinnamate, methanesulfonic acid salt, benzenesulfonic acid salt, p-toluenesulfonic acid salt or salicylic acid salt. The appropriate alkali or organic ammonium salts which can be used include, for example, potassium salt, sodium salt, calcium salt, magnesium salt, barium salt or ammonium salt.

PREPARATION EXAMPLE

The compounds of the present invention may be prepared by the following procedure.

The compounds of the present invention with the formula I may be prepared by reacting quinoline-4(1H)-thione derivatives (the formula VII) with halide (the formula VIII) as shown in the following reaction formula. In this reaction, base may be employed as needs demands. Such base may include potassium carbonate, sodium hydroxide, sodium hydride, barium oxide, triethylamine or the like. Reaction solvent which can be used include DMSO, DMF, THF, acetone, ether or the like. Reaction time may be selected according to a reaction temperature range of −10° C. to boiling point of the solvent, and usually be 0.5–20 hours under the reaction temperature range of 0–50° C.

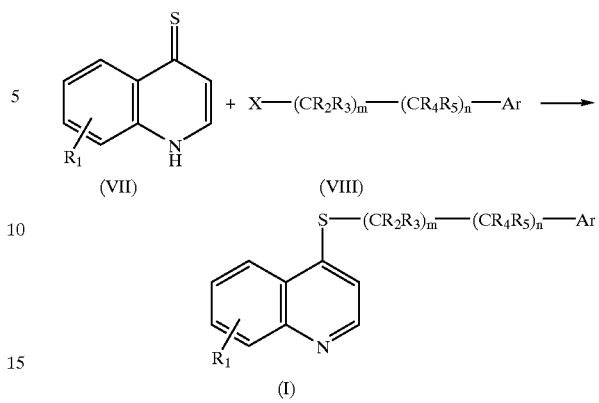

wherein X represents clorine or bromine atom and $R_1$, $R_2$, $R_3$, $R_4$, $R_5$, Ar, m and n are as defined above.

The compounds of the present invention thus obtained may be used as starting materials to prepare corresponding derivatives through alkylation, acylation, hydrolysis, reduction or the like according to the prior art.

The compounds of the present invention thus obtained may be separated and purified by a usual manner such as extraction, condensation, neutralization, filtration, recrystallization or column chromatography, if necessary.

Pharmaceutically acceptable salts of the compounds of the present invention may be prepared by various known methods in the art.

The compounds of the formula VII which are the starting materials in the above-mentioned process are known compounds the preparation of which is disclosed in WO 96/11187. The compounds of the formula VIII are commercially available and alternatively can be readily synthesized according to a process described for example in Chem. Pharm. Bull. 39: 1751 (1991), J. Org. Chem. 27: 4397 (1962), 29: 3459 (1964) and 40: 1990 (1975), Org. Syn. Coll. 6: 711, Reagents for Organic Synthesis 1: 967.

Next, described is antibacterial activity of the compound of the present invention represented by the formula I. The numbers of test compounds in Antibacterial Tests 1 and 2 correspond to those in Examples referred to hereinafter. Controls used were antibiotic (amoxicillin and clarithromycin) and anti-ulcer agent (lansoprazole) having antibacterial activity against Hp.

Antibacterial Test 1

Antibacterial test against Hp was performed in substantial accordance with agar plate dilution method (anaerobic MIC method) based on standard method of the Japan Society of Chemotherapy to determine minimum inhibitory concentration (MIC) of the respective test compounds.

[Preparation of Medium for Sensitivity Testing]

The respective test compounds were dissolved in dimethyl sulfoxide (DMSO) and serially diluted twofold to prepare diluted solutions of the compounds with concentration of 0.000025–100 μg/ml. The solutions of the compounds are respectively added to brucella agar medium (prepared by Difco) containing 7% horse blood free from fibrin (prepared by NIPPON BIOTEST KENKYUSHO) to prepare agar plates for determination.

[Preparation of Inocula]

Strain used for inoculation was *Helicobacter pylori* standard strain ATCC 43526 (NCTC 11916). For pre-culturing of bacteria to be inoculated, the above-mentioned strain freezingly conserved at −135° C. was thawed in a warm bath (40° C.), applied on a brucella agar medium containing 7% horse blood free from fibrin, and microaerobically cultured in a jar for anaerobic bacteria at 37° C. for 3 days. The suspension of bacteria to be inoculated was prepared by collecting colonies grown on the culture medium and suspending the same in the brucella broth.

The suspension was made such that the concentration of the bacteria to be inoculated provides absorbancy $O.D_{570nm}=0.50$, and $2.0\times10^7$ CFU/ml of the suspension of the bacteria was prepared, then 5 μl of which was inoculated with multi-inoculator (manufactured by SAKUMA SEISAKUSHO). Culturing was performed for 3 days under the same conditions as those of the pre-culturing and the MIC (unit: μg/ml) was determined by observing whether the bacteria grew or not. The obtained results are shown in Table 1.

added to sensitive-disk agar medium-N (manufactured by NISSUI SEIYAKU) to prepare agar plates for determination.

[Preparation of Inocula]

Strains used for inoculation were 7 species as shown in Table 2. The below-mentioned strains freezingly conserved at −135° C. were thawed in a warm bath (40° C.), cultured in a sensitivity-determining bouillon at 37° C. for 18–20 hours, and then diluted with the above-mentioned medium to prepare about $1.0\times10^6$ CFU/ml of bacterial suspension.

Inoculation was made by 5 μl by multi-inoculator (manufactured by SAKUMA SEISAKUSHO). Culturing was made under the same conditions as those of the pre-culturing and the MIC (unit: μg/ml) was determined by observing whether the bacteria grew or not. The obtained results are shown in Tables 2 to 6.

TABLE 1

| Test Compound | MIC (μg/ml) | Test Compound | MIC (μg/ml) | Test Compound | MIC (μg/ml) |
|---|---|---|---|---|---|
| Compound 1 | 0.05 | Compound 36 | 0.10 | Compound 66 | 0.0004 |
| Compound 2 | 0.20 | Compound 37 | 0.20 | Compound 67 | 0.0062 |
| Compound 4 | 0.10 | Compound 38 | 0.20 | Compound 68 | 0.0016 |
| Compound 5 | 0.025 | Compound 39 | 0.10 | Compound 69 | 0.025 |
| Compound 6 | 0.05 | Compound 40 | 0.20 | Compound 70 | 0.05 |
| Compound 10 | 0.0031 | Compound 41 | 0.20 | Compound 71 | 0.05 |
| Compound 11 | 0.0125 | Compound 43 | 0.10 | Compound 72 | 0.05 |
| Compound 14 | 0.0016 | Compound 44 | 0.20 | Compound 73 | 0.0062 |
| Compound 15 | 0.10 | Compound 45 | 0.20 | Compound 74 | 0.0008 |
| Compound 17 | 0.05 | Compound 46 | 0.10 | Compound 75 | 0.0125 |
| Compound 19 | 0.10 | Compound 47 | 0.20 | Compound 76 | 0.0062 |
| Compound 20 | 0.025 | Compound 48 | 0.10 | Compound 78 | 0.0031 |
| Compound 22 | 0.0062 | Compound 49 | 0.0008 | Compound 79 | 0.0016 |
| Compound 23 | 0.025 | Compound 50 | 0.05 | Compound 81 | 0.0016 |
| Compound 24 | 0.20 | Compound 51 | 0.20 | Compound 82 | 0.0008 |
| Compound 25 | 0.10 | Compound 52 | 0.0008 | Compound 83 | 0.0008 |
| Compound 26 | 0.10 | Compound 53 | 0.025 | Compound 84 | 0.0016 |
| Compound 27 | 0.10 | Compound 54 | 0.0016 | Compound 85 | 0.0031 |
| Compound 28 | 0.0008 | Compound 55 | 0.0062 | Compound 86 | 0.0031 |
| Compound 29 | 0.0008 | Compound 56 | 0.0125 | Compound 87 | 0.0008 |
| Compound 30 | 0.10 | Compound 57 | 0.39 | clarithromycin | 0.025 |
| Compound 31 | 0.10 | Compound 58 | 0.0031 | amoxicillin | 0.05 |
| Compound 33 | 0.20 | Compound 61 | 0.20 | lansoprazole | 12.5 |
| Compound 34 | 0.20 | Compound 63 | 0.10 | | |
| Compound 35 | 0.39 | Compound 65 | 0.0031 | | |

As is clear from the above Table 1, the compounds of the present invention exhibit excellent antibacterial activities against Hp and some of them have activities superior to those of amoxicillin and clarithromycin. Structurally, the compounds of the formula I wherein m and n are respective 1, $CR_4R_5$ is carbonyl, all of $R_1$, $R_2$ and $R_3$ are hydrogen atoms, and Ar is a group of the formula VI exhibited especially excellent activities.

Antibacterial Test 2

Then, tested were antibacterial activities of the typical compounds of the present invention against gram-positive and -negative bacteria other than Hp. MICs of the typical compounds of the present invention were determined in substantial accordance with agar dilution method (aerobic MIC method) based on standard method of the Japan Society Chemotherapy.

[Preparation of Medium for Sensitivity Testing]

The respective test compound were dissolved in dimethyl sulfoxide (DMSO) and serially diluted twofold to prepare solutions of the compounds with concentration of 0.05–100 μg/ml. The solutions of the compounds were respectively

TABLE 2

| | MIC (μg/ml) | | |
|---|---|---|---|
| Strain | Compound 1 | Compound 2 | Compound 5 |
| S. aureus FDA 209P | >100 | >100 | >100 |
| M. luteus ATCC 9341 | >100 | >100 | >100 |
| E. faecalis RIMD 3336001 | >100 | >100 | >100 |
| B. subtilis PCI 219 | >100 | >100 | >100 |
| E. coli NIHJ JC-2 | >100 | >100 | >100 |
| K. pneumoniae PCI 602 | >100 | >100 | >100 |
| P. aeruginosa IFO 3445 | >100 | >100 | >100 |

TABLE 3

| Strain | MIC (μg/ml) | | |
|---|---|---|---|
| | Compound 10 | Compound 11 | Compound 22 |
| S. aureus FDA 209P | >100 | >100 | >100 |
| M. luteus ATCC 9341 | >100 | >100 | >100 |
| E. faecalis RIMD 3336001 | >100 | >100 | >100 |
| B. subtilis PCI 219 | >100 | >100 | >100 |
| E. coli NIHJ JC-2 | >100 | >100 | >100 |
| K. pneumoniae PCI 602 | >100 | >100 | >100 |
| P. aeruginosa IFO 3445 | >100 | >100 | >100 |

TABLE 4

| Strain | MIC (μg/ml) | | |
|---|---|---|---|
| | Compound 23 | Compound 26 | Compound 27 |
| S. aureus FDA 209P | >100 | >100 | 50 |
| M. luteus ATCC 9341 | >100 | >100 | >100 |
| E. faecalis RIMD 3336001 | >100 | >100 | >100 |
| B. subtilis PCI 219 | >100 | >100 | >100 |
| E. coli NIHJ JC-2 | >100 | >100 | >100 |
| K. pneumoniae PCI 602 | >100 | >100 | >100 |
| P. aeruginosa IFO 3445 | >100 | >100 | >100 |

TABLE 5

| Strain | MIC (μg/ml) | | |
|---|---|---|---|
| | Compound 31 | Compound 34 | Compound 49 |
| S. aureus FDA 209P | >100 | >100 | >100 |
| M. luteus ATCC 9341 | >100 | >100 | >100 |
| E. faecalis RIMD 3336001 | >100 | >100 | >100 |
| B. subtilis PCI 219 | >100 | >100 | >100 |
| E. coli NIHJ JC-2 | >100 | >100 | >100 |
| K. pneumoniae PCI 602 | >100 | >100 | >100 |
| P. aeruginosa IFO 3445 | >100 | >100 | >100 |

TABLE 6

| Strain | MIC (μg/ml) | | |
|---|---|---|---|
| | Amoxicillin | Clarithromycin | Lansoprazole |
| S. aureus FDA 209P | 0.10 | 0.10 | >100 |
| M. luteus ATCC 9341 | ≦0.05 | ≦0.05 | >100 |
| E. faecalis RIMD 3336001 | 0.20 | 0.39 | >100 |
| B. subtilis PCI 219 | 0.20 | 0.20 | >100 |
| E. coli NIHJ JC-2 | 3.13 | 100 | >100 |
| K. pneumoniae PCI 602 | 50 | 6.25 | >100 |
| P. aeruginosa IFO 3445 | >100 | >100 | >100 |

The antibacterial activities of the compounds 65, 67–70, 73–76, 78, 79, 81, 83–85 of the present invention were determined in the manner same as the above to find out that MIC of each of the above-mentioned seven strains is more than 100 μg/ml.

As is clear from the above test results, the typical compounds of the present invention hardly exhibit antibacterial activity against the above-mentioned seven gram-positive or -negative strains. This means that the compounds of the present invention has selective antibacterial activity against Hp.

Thus, the compounds of the present invention have selective and effective antibacterial activities against the genus Helicobacter represented by Hp and have no antibacterial activities against intestinal bacteria such as E. coli, hardly cause any fluctuation of intestinal bacterial flora which may be caused in the case of other antibacterial agents such as penicillin and cephalosporin and are less dangerous of causing side effects such as enteritis and pseudomembranous colitis based on microbial substitution. Moreover, the compounds of the present invention exhibit the antibacterial activity selectively against the genus Helicobacter, so that they are deemed to hardly cause resistance induction for other strains, which is frequently seen in the case of existing antibacterial agents such as β-lactams and macrolides, as well as cross-resistance with other antibacterial agents.

Therefore, the compounds of the present invention can be applied as selective antibacterial agent against Hp for the treatment and prevention of recurrence of peptic ulcer and chronic gastritis with Hp infection. The compounds of the present invention may be administered to human orally or parenterally. In oral administration, the compounds may be in the form of tablets, coated tablets, powders, granules, capsules, microcapsules, syrups and the like; and in parenteral administration, in the form of injections which may include soluble freeze-drying form, suppositories and the like. In the preparation of these forms, pharmaceutically acceptable diluent bases, binders, lubricants, disintegrators, suspensions, emulsifiers, antiseptics, stabilizers and dispersing agents, for example, lactose, sucrose, starch, dextrin, crystalline cellulose, kaolin, calcium carbonate, talc, magnesium stearate, distilled water and physiological saline solution may be used.

BEST MODE FOR CARRYING OUT THE INVENTION

EXAMPLES

Next, Examples will be explained to detailedly disclose the present invention. However, it is to be noted that the present invention is not limited to the Examples.

Example 1
4-[2-(4-Benzyloxyphenyl)-2-oxoethylthio]quinoline (Compound 1)

Quinoline-4(1H)-thione (3.50 g, 21.9 mmol) and potassium carbonate (3.95 g, 28.5 mmol) were suspended in dry acetone(350 ml). 1-Benzyloxy-4-bromoacetylbenzene (8.00 g, 26.3 mmol) was gradually added to the suspension under ice cooling and stirred at room temperature overnight. The solvent was removed under reduced pressure. The residue was added with water, extracted with ethyl acetate, washed with saturated saline solution, and dried over anhydrous magnesium sulfate. The solvent was removed under reduced pressure. The residue was chromatographed by silica gel column chromatography (n-hexane:ethyl acetate=1:4) and recrystallized from ethyl acetate to obtain 5.43 g of the titled compound (64.4%) as yellow-white crystal.

Melting Point: 135.0–136.5° C.; MS m/z: 385 (M$^+$); NMR(CDCl$_3$) δ: 4.53(2H, s), 5.13(2H, s), 7.06(2H, d, J=8.9 Hz), 7.3–7.5(6H, m), 7.59(1H, brt, J=7.2 Hz), 7.76(1H, brt, J=7.2 Hz), 8.02(2H, d, J=8.9 Hz), 8.17(2H, brt, J=8.6 Hz), 8.71(1H, d, J=5.0 Hz)

In accordance with the procedure of the Example 1, the following compounds were obtained from corresponding starting materials.

4-[2-(2-Naphtyl)-2-oxoethylthio]quinoline (Compound 2)

MS m/z: 329 (M+); NMR(CDCl$_3$) δ: 4.65(2H, s), 7.32 (1H, d, J=5.0 Hz), 7.5–7.8(4H, m), 7.8–8.0(3H, m), 8.0–8.1 (2H, m), 8.16(1H, dd, J=1.2, 8.4 Hz), 8.53(1H, brs), 8.72 (1H, d, J=5.0 Hz)

4-[2-(2-Fluorenyl)-2-oxoethylthio]-7-methoxyquinoline (Compound 3)

MS m/z: 397 (M+); NMR(CDCl$_3$) δ: 3.96(3H, s), 3.99 (2H, s), 4.62(2H, s), 7.2–7.25(2H, m), 7.4–7.5(3H, m), 7.6–7.7(1H, m), 7.8–8.0(2H, m), 8.09(2H, d, J=9.2 Hz), 8.20(1H, brs), 8.64(1H, d, J=5.0 Hz)

4-[2-(p-Biphenyl)-2-oxoethylthio]quinoline (Compound 4)

MS m/z: 355 (M+); NMR(CDCl$_3$) δ: 4.60(2H, s), 7.35 (1H, d, J=5.0 Hz), 7.4–7.55(3H, m), 7.55–7.7(3H, m), 7.7–7.8(3H, m), 8.1–8.25(4H, m), 8.74(1H, d, J=5.0 Hz)

4-[2-(4-tert-Butylphenyl)-2-oxoethylthio]quinoline (Compound 5)

MS m/z: 335 (M+); NMR(CDCl$_3$) δ: 1.36(9H, s), 4.57 (2H, s), 7.30(1H, d, J=5.0 Hz), 7.53(2H, d, J=8.6 Hz), 7.58(1H, ddd, J=1.3, 6.9, 8.3 Hz), 7.72(1H, ddd, J=1.3, 6.9, 8.3 Hz), 7.98(2H, d, J=8.9 Hz), 8.07(1H, dd, J=0.7, 8.6 Hz), 8.17(1H, dd, J=0.7, 8.3 Hz), 8.72(1H, d, J=5.0 Hz)

4-[2-(2,4-Dimethoxyphenyl)-2-oxoethylthio]quinoline (Compound 6)

MS m/z: 339 (M+); NMR(CDCl$_3$) δ: 3.87(3H, s), 3.98 (3H, s), 4.55(2H, s), 6.50(1H, d, J=2.3 Hz), 6.57(1H, dd, J=2.3, 8.9 Hz), 7.28(1H, d, J=5.0 Hz), 7.53(1H, ddd, J=1.2, 7.0, 8.7 Hz), 7.70(1H, ddd, J=1.2, 6.9, 8.2 Hz), 7.91(1H, d, J=5.0 Hz), 8.05(1H, brd, J=8.6 Hz), 8.16(1H, dd, J=1.0, 8.6 Hz), 8.69(1H, d, J=5.0 Hz)

4-[2-[4-[2-(4-tert-Butylphenyl)-2-oxoethoxy]phenyl]-2-oxoethylthio]quinoline (Compound 7)

MS m/z: 469 (M+); NMR(CDCl$_3$) δ: 1.36(9H, s), 4.50 (2H, s), 5.38(2H, s), 7.01(2H, d, J=8.9 Hz), 7.28(1H, d, J=4.6 Hz), 7.5–7.55(3H, m), 7.72(1H, ddd, J=1.3, 6.6, 8.3 Hz), 7.94(2H, d, J=8.6 Hz), 8.01(2H, d, J=8.9 Hz), 8.07(1H, brd, J=8.6 Hz), 8.16(1H, d, J=8.2 Hz), 8.72(1H, d, J=4.6 Hz)

4-[3-(4-Methoxyphenyl)-3-oxopropylthio]quinoline (Compound 8)

MS m/z: 323 (M+); NMR(CDCl$_3$) δ: 3.45(2H, brt, J=7.6 Hz), 3.57(2H, brt, J=7.2 Hz), 3.87(3H, s), 6.94(2H, d, J=8.9 Hz), 7.31(1H, d, J=5.0 Hz), 7.58(1H, brt, J=7.9 Hz), 7.76 (1H, brt, J=8.3 Hz), 7.95(2H, d, J=8.9 Hz), 8.15(2H, m), 8.74(1H, d, J=5.0 Hz)

4-[2-(4-Phenoxyphenyl)-2-oxoethylthio]quinoline (Compound 9)

MS m/z: 371 (M+); NMR(CDCl$_3$) δ: 4.52(2H, s), 7.04 (2H, d, J=8.9 Hz), 7.09(2H, d, J=7.6 Hz), 7.22(1H, brd, J=7.3 Hz), 7.33(1H, d, J=5.0 Hz), 7.42(2H, brt, J=7.9 Hz), 7.59(1H, brt, J=7.4 Hz), 7.75(1H, brt, J=7.3 Hz), 8.02(2H, d, J=8.9 Hz), 8.16(2H, brt, J=9.9 Hz), 8.72(1H, d, J=5.0 Hz)

4-[2-(3-Bromo-4-morpholinophenyl)-2-oxoethylthio]-quinoline (Compound 10)

MS m/z: 443 (M+); NMR(CDCl$_3$) δ: 3.19(4H, brt, J=4.6 Hz), 3.90(4H, brt, J=4.6 Hz), 4.52(2H, s), 7.07(11, d, J=8.6 Hz), 7.2–7.3(1H, m), 7.36(1H, d, J=4.6 Hz), 7.63(1H, brt, J=7.8 Hz), 7.79(1H, brt, J=7.8 Hz), 7.96(1H, dd, J=2.1, 8.6 Hz), 8.19(1H, brd, J=8.9 Hz), 8.23(1H, d, J=2.0 Hz), 8.72 (1H, d, J=5.0 Hz)

4-[2-(4-Morpholinophenyl)-2-oxoethylthio]quinoline (Compound 11)

MS m/z: 364 (M+); NMR(CDCl$_3$) δ: 3.35(4H, brt, J=5.0 Hz), 3.87(4H, brt, J=5.0 Hz), 4.50(2H, s), 6.89(2H, d, J=8.9 Hz), 7.34(1H, d, J=5.0 Hz), 7.57(1H, ddd, J=1.3, 6.9, 8.3 Hz), 7.74(1H, ddd, J=1.3, 6.9, 8.6 Hz), 7.97(2H, d, J=8.9 Hz), 8.12(1H, brd, J=8.3 Hz), 8.18(1H, d, J=8.3 Hz), 8.71 (1H, d, J=5.0 Hz)

4-[2-(4-Hydroxy-2-methoxyphenyl)-2-oxoethylthio] quinoline (Compound 12)

MS m/z: 325 (M+); NMR(CD$_3$OD-CDCl$_3$) δ: 3.98(3H, s), 4.58(2H, s), 6.45–6.52(2H, m), 7.30(1H, d, J=5.3 Hz), 7.57(1H, ddd, J=1.0, 6.6, 8.3 Hz), 7.73(1H, ddd, J=1.7, 6.9, 8.6 Hz), 7.82(1H, d, J=9.2 Hz), 8.01(1H, brd, J=7.6 Hz), 8.19(1H, dd, J=0.8, 8.3 Hz), 8.60(1H, d, J=4.9 Hz)

4-[3-(4-Acetoaminophenyl)-3-oxopropylthio]quinoline (Compound 13)

MS m/z: 350 (M+); NMR(CDCl$_3$) δ: 2.22(3H, s), 3.4–3.6 (4H, m), 7.27(1H, d, J=4.6 Hz), 7.46(1H, brs), 7.55(1H, ddd, J=1.0, 6.9, 8.2 Hz), 7.62(2H, d, J=8.6 Hz), 7.72(1H, ddd, J=1.6, 6.9, 8.6 Hz), 7.94(2H, d, J=8.9 Hz), 8.07(1H, d, J=8.6 Hz), 8.10(1H, d, J=8.6 Hz), 8.74(1H, d, J=5.0 Hz)

4-[2-[3-Bromo-4-(4-tert-butoxycarbonyl-1-piperazinyl)-phenyl]-2-oxoethylthio]quinoline (Compound 14)

MS m/z: 541 (M+); NMR(CDCl$_3$) δ: 1.49(9H, s), 3.11 (4H, brt, J=4.9 Hz), 3.63(4H, brt, J=5.0 Hz), 4.46(2H, s), 7.04(1H, d, J-8.6 Hz), 7.30(1H, d, J=5.0 Hz), 7.56(1H, ddd, J=1.3, 6.9, 8.2 Hz), 7.73(1H, ddd, J=1.6, 6.9, 8.3 Hz), 7.94(1H, dd, J=2.2, 8.3 Hz), 8.08(1H, d, J=8.3 Hz), 8.16(1H, dd, J=1.0, 8.6 Hz), 8.22(1H, d, J=2.3 Hz), 8.73(1H, d, J=4.6 Hz)

4-[2-[4-(4-Methoxyphenoxy)phenyl]-2-oxoethylthio]-quinoline (Compound 15)

MS m/z: 401 (M+); NMR(CDCl$_3$) δ: 3.83(3H, s), 4.52 (2H, s), 6.9–7.1(6H, m), 7.33(1H, d, J=5.0 Hz), 7.59(1H, ddd, J=1.3, 6.9, 8.3 Hz), 7.76(1H, ddd, J=1.3, 6.9, 8.3 Hz), 8.00(2H, d, J=9.2 Hz), 8.1–8.2(2H, m), 8.72(1H, d, J=5.0 Hz)

4-[1,1-Dimethyl-2-(4-methoxyphenyl)-2-oxoethylthio]-quinoline (Compound 16)

MS m/z: 337 (M+); NMR(CDCl$_3$) δ: 1.75(6H, s), 3.83 (3H, s), 6.90(2H, d, J=9.2 Hz), 7.23(1H, d, J=4.6 Hz), 7.59(1H, ddd, J=1.3, 6.4, 8.2 Hz), 7.72(1H, ddd, J=1.3, 6.9, 8.6 Hz), 8.11(1H, brd, J=8.3 Hz), 8.34(1H, dd, J=2.0, 7.3 Hz), 8.36(2H, d, J=9.2 Hz), 8.64(1H, d, J=4.6 Hz)

4-(2-(3,4,5-Trimethoxyphenyl)-2-oxoethylthio]quinoline (Compound 17)

MS m/z: 369 (M+); NMR(CDCl$_3$) δ: 3.92(6H, s), 3.95 (3H, s), 4.53(2H, s), 7.27(2H, s), 7.34(1H, d, J=5.0 Hz), 7.59(1H, ddd, J=1.3, 6.9, 8.3 Hz), 7.76(1H, ddd, J=1.3, 6.9, 8.6 Hz), 8.15(1H, brd, J=8.6 Hz), 8.19(1H, dd, J=1.0, 8.6 Hz), 8.73(1H, d, J=4.6 Hz)

4-[2-(4-Hydroxy-3-methoxyphenyl)-2-oxoethylthioo] quinoline

MS m/z: 325 (M+); NMR(CD$_3$OD-CDCl$_3$) δ: 3.95(3H, s), 4.64(2H, s), 6.96(2H, d, J=9.2 Hz), 7.41(1H, d, J=5.0 Hz), 7.58(1H, d, J=2.0 Hz), 7.6–7.7(2H, m), 7.81(1H, ddd, J=1.3, 6.9, 8.6 Hz), 8.09(1H, d, J=8.3 Hz), 8.24(1H, d, J=8.2 Hz), 8.68(1H, brs)

4-[2-(3-Benzyloxyphenyl)-2-oxoethylthio]quinoline (Compound 18)

MS m/z: 385 (M+); NMR(CDCl$_3$) δ: 4.53(2H, s), 5.12 (2H, s), 7.22–7.24(1H, m), 7.29(1H, d, J=4.6 Hz), 7.31–7.46 (6H, m), 7.54–7.64(3H, m), 7.74(1H, dd, J=7.1, 8.3 Hz)t 8.11(1H, d, J=8.3 Hz), 8.17(1H, d, J=8.3 Hz), 8.72(1H, d, J=4.6 Hz)

4-[2-(4-Pivaloylaminophenyl)-2-oxoethylthio]quinoline (Compound 19)

MS m/z: 378 (M+); NMR(CDCl$_3$) δ: 1.34(9H, s), 4.52 (2H, s), 7.30(1H, d, J=4.6 Hz), 7.52–7.59(2H, m), 7.70(2H, d, J=8.7 Hz), 7.73(1H, dd, J=6.9, 8.3 Hz), 8.02(2H, d, J=8.7 Hz), 8.07(1H, d, J=8.3 Hz), 8.16(1H, d, J=8.3 Hz), 8.72(1H, d, J=4.6 Hz)

4-[2-(4-Benzylamino-3-bromophenyl)-2-oxoethylthio]-quinoline (Compound 20)

MS m/z: 462 (M+); NMR(CDCl$_3$) δ: 4.42(2H, s), 4.50 (2H, d, J=5.5 Hz), 5.42(1H, brt, J=5.5 Hz), 6.61(1H, d, J=8.6 Hz), 7.29(1H, d, J=4.6 Hz), 7.31–7.42(5H, m), 7.55(1H, dd, J=6.9, 8.3 Hz), 7.72(1H, dd, J=6.9, 8.3 Hz), 7.84(1H, dd, J=2.0, 8.6 Hz), 8.07(1H, d, J=8.3 Hz), 8.16(1H, d, J=8.3 Hz), 8.17(1H, d, J=2.0 Hz), 8.71(1H, d, J=4.6 Hz)

4-[2-[4-(N-Acetylbenzylamino)phenyl]-2-oxoethylthio]-quinoline (Compound 21)

MS m/z: 426 (M+); NMR(CDCl$_3$) δ: 1.96(3H, s), 4.50 (2H, s), 4.94(2H, s), 7.15–7.22(3H, m), 7.24–7.28(4H, m), 7.30(1H, d, J=4.6 Hz), 7.57(1H, dd, J=7.0, 8.3 Hz), 7.74(1H, dd, J=7.0, 8.3 Hz), 7.99(2H, d, J=8.6 Hz), 8,10(1H, d, J=8.3 Hz), 8.15(1H, d, J=8.3 Hz), 8.72(1H, d, J=4.6 Hz)

4-[2-(4-Piperidinophenyl)-2-oxoethylthio]quinoline (Compound 22)

MS m/z: 362 (M+); NMR(CDCl$_3$) δ: 1.68(6H, brs), 3.40 (4H, brs), 4.47(2H, s), 6.86(2H, d, J=9.2 Hz), 7.31(1H, d, J=4.8 Hz), 7.55(1H, dd, J=6.9, 8.3 Hz), 7.71(1H, dd, J=6.9, 8.3 Hz), 7.93(2H, d, J=9.2 Hz), 8.06(1H, d, J=8.3 Hz), 8.18(1H, d, J=8.3 Hz), 8.71(1H, d, J=4.8 Hz)

4-[2-(4-Benzylaminophenyl)-2-oxoethylthio]quinoline (Compound 23)

MS m/z: 384 (M+); NMR(CDCl$_3$) δ: 4.42(2H, d, J=5.4 Hz), 4.45(2H, s), 4.76(1H, brt, J=5.4 Hz), 6.63(2H, d, J=8.9 Hz), 7.29(1H, d, J=4.6 Hz), 7.31–7.40(5H, m), 7.54(1H, dd, J=7.0, 8.4 Hz), 7.71(1H, dd, J=7.0, 8.4 Hz), 7.90(2H, d, J=8.9 Hz), 8.06(1H, d, J=8.4 Hz), 8.17(1H, d, J=8.4 Hz), 8.70(1H, d, J=4.6 Hz)

4-[2-(4-tert-Butoxycarbonylaminophenyl)ethylthio]-quinoline (Compound 24)

MS m/z: 380 (M+); NMR(CDCl$_3$) δ: 1.52(9H, s), 3.04 (2H, m), 3.33(2H, m), 6.45(1H, s), 7.15–7.20(3H, m), 7.32 (2H, d, J=8.3 Hz), 7.54(1H, m), 7.71(1H, m), 8.05–8.13(2H, m), 8.72(1H, d, J=5.0 Hz)

4-[2-(4-Benzyloxyphenyl)ethylthio]quinoline (Compound 25)

MS m/z: 371 (M+); NMR(CDCl$_3$) δ: 3.05(2H, t, J=7.5 Hz), 3.38(2H, t, J=7.5 Hz), 5.06(2H, s), 6.95(2H, d, J=8.9 Hz), 7.15–7.45(8H, m), 7.60(1H, m), 7.75(1H, m), 8.15(2H, m), 8.70(1H, d, J=4.9 Hz)

4-[2-(4-Dimethylaminophenyl)-2-oxoethylthio]quinoline (Compound 26)

MS m/z: 322 (M+); NMR(CDCl$_3$) δ: 3.06(6H, s), 4.47 (2H, s), 6.68(2H, d, J=8.9 Hz), 7.32(1H, d, J=4.9 Hz), 7.54(1H, m), 7.71(1H, m), 7.95(2H, d, J=9.2 Hz), 8.05(1H, d, J=8.2 Hz), 8.17(1H, dd, J=1.0, 8.2 Hz), 8.71(1H, d, J=4.6 Hz)

4-[2-(4-Dimethylaminophenyl)ethylthio]quinoline (Compound 27)

MS m/z: 308 (M+); NMR(CDCl$_3$) δ: 2.94(6H, s), 3.00 (2H, m), 3.32(2H, m), 6.72(2H, d, J=8.9 Hz), 7.15(2H, d, J=8.9 Hz), 7.20(1H, d, J=4.9 Hz), 7.53(1H, m), 7.72(1H, m), 8.04–8.15(2H, m), 8.71(1H, d, J=4.9 Hz)

4-[2-[4-(1-Pivaloyl-4-piperidinyl)phenyl]-2-oxoethylthio]-quinoline (Compound 28)

MS m/z: 446 (M+); NMR(CDCl$_3$) δ: 1.32(9H, s), 1.57–1.73(2H, m), 1.92(2H, brd, J=11.5 Hz), 2.80–2.94(3H, m), 4.52(2H, s), 4.61(2H, brd, J=13.5 Hz), 7.30(1H, d, J=4.6 Hz), 7.34(2H, d, J=8.2 Hz), 7.56(1H, dd, J=7.0, 8.3 Hz), 7.72(1H, dd, J=7.0, 8,3 Hz), 7.99(2H, d, J=8.2 Hz), 8.07(1H, d, J=8.3 Hz), 8.16(1H, d, J=8.3 Hz), 8.72(1H, d, J=4.6 Hz)

4-[2-[4-(4-Isobutyl-1-piperazinyl)phenyl]-2-oxoethylthio]quinoline (Compound 29)

MS m/z: 419 (M+); NMR(CDCl$_3$) δ: 0.93(6H, t, J=6.6 Hz), 1.81(1H, m), 2.14(2H, d, J=7.6 Hz), 3.54(4H, t, J=5.0 Hz), 3.40(4H, t, J=5.0 Hz), 4.48(2H, s), 6.88(2H, d, J=8.9 Hz), 7.31(1H, d, J=5.0 Hz), 7.55(1H, t, J=7.8 Hz), 7.71(1H, t, J=7.8 Hz), 7.95(2H, d, J=8.6 Hz), 8.07(1H, d, J=8.3 Hz), 8.17(1H, d, J=8.9 Hz), 8.71(1H, d, J=4.6 Hz)

4-[2-(4-tert-Butoxycarbonylaminophenyl)-2-oxoethylthio]-quinoline (Compound 30)

MS m/z: 394 (M+); NMR(CDCl$_3$) δ: 1.53(9H, s), 4.51 (2H, s), 6.75(1H, s), 7.29(1H, d, J=4.9 Hz), 7.45–7.55(3H, m), 7.70(1H, m), 7.90–8.20(4H, m), 8.72(1H, d, J=4.9 Hz)

4-[4-(4-Formyl-1-piperazinylmethyl)benzylthio]-7-methylthioquinoline (Compound 64)

MS m/z: 423 (M+); NMR(CDCl$_3$) δ: 2.42(4H, m), 2.60 (3H, s), 3.38(2H, m), 3.47(2H, s), 3.56(2H, m), 4.31(2H, s), 7.14(1H, d, J=5.0 Hz), 7.27–7.41(5H, m), 7.75(1H, d, J=2.0 Hz), 7.98(1H, d, J=8.6 Hz), 8.02(1H, s), 8.62(1H, d, J=5.0 Hz)

4-[2-[3-Bromo-4-(1-tert-butoxycarbonyl-3-pyrrolidinylamino)phenyl]-2-oxoethylthio]quinoline (Compound 65)

MS m/z: 541 (M+); NMR(CDCl$_3$) δ: 1.46(9H, s), 1.9–2.0 (1H, m), 2.2–2.3(1H, m), 3.49(1H, dd, J=3.9, 10.3 Hz), 3.5–3.6(1H, m), 3.7–3.8(2H, m), 4.33(1H, brs), 4.44(2H, s), 4.73(1H, brs), 6.77(1H, d, J=8.8 Hz), 7.31(1H, d, J=5.0 Hz), 7.56(1H, ddd, J=1.5, 6.8, 8.3 Hz), 7.72(1H, ddd, J=1.5, 6.8, 8.3 Hz), 7.84(1H, dd, J=2.0, 8.8 Hz), 8.07(1H, d, J=8.3 Hz), 8.17(2H, m), 8.72(1H, d, J=5.0 Hz)

4-[2-[3-Bromo-4-(4-neopentyl-1-piperazinyl)phenyl]-2-oxoethylthio]quinoline (Compound 66)

MS m/z: 511 (M+); NMR(CDCl$_3$) δ: 0.90(9H, s), 2.15 (2H, s), 2.73(4H, t, J=4.8 Hz), 3.17(4H, t, J=4.6 Hz), 4.46(2H, s), 7.05(1H, d, J=8.6 Hz), 7.30(1H, d, J=5.0 Hz), 7.56(1H, ddd, J=1.3, 6.9, 8.2 Hz), 7.72(1H, ddd, J=1.3, 6.9, 8.3 Hz), 7.92(1H, dd, J=2.3, 8.6 Hz), 8.08(1H, d, J=8.3 Hz), 8.16(1H, d, J=8.3 Hz), 8.20(1H, d, J=2.3 Hz), 8.73(1H, d, J=5.0 Hz)

4-[2-[4-[4-(4-Bromophenyl)-1-piperazinyl]phenyl]-2-oxoethylthio]quinoline (Compound 67)

MS m/z: 517 (M+); NMR(CDCl$_3$) δ: 3.32(4H, dd, J=0.7, 5.0 Hz), 3.56(4H, dd, J=4.6, 6.9 Hz), 4.48(2H, s), 6.82(2H, d, J=9.2 Hz), 6.93(2H, d, J=8.9 Hz), 7.32(1H, d, J=4.6 Hz), 7.38(2H, d, J=8.9 Hz), 7.55(1H, ddd, J=1.3, 6.9, 8.2 Hz), 7.72(1H, ddd, J=1.3, 6.9, 8.3 Hz), 7.98(2H, d, J=9.2 Hz), 8.07(1H, d, J=8.3 Hz), 8.17(1H, dd, J=0.7, 8.3 Hz), 8.71(1H, d, J=4.6 Hz)

4-[2-[4-[4-(2-Pyrimidyl)-1-piperazinyl]phenyl]-2-oxoethylthio]quinoline (Compound 68)

MS m/z: 441 (M+); NMR(DMSO-d$_6$) δ: 3.48(4H, t, J=5.1 Hz), 3.83(4H, t, J=5.1 Hz), 5.22(2H, s), 6.63(1H, t, J=4.5 Hz), 7.02(2H, d, J=8.9 Hz), 7.82(1H, d, J=5.9 Hz), 7.89(1H, t, J=7.4 Hz), 7.97(2H, d, J=8.9 Hz), 8.00–8.20(2H, m), 8.35(2H, d, J=4.6 Hz), 8.40(1H, d, J=8.6 Hz), 8.97(1H, d, J=5.9 Hz)

4-[2-[4-(Heptylamino)phenyl]-2-oxoethylthio]quinoline (Compound 69)

MS m/z: 392 (M+); NMR(CDCl$_3$) δ: 0.89(3H, t, J=6.9 Hz), 1.2–1.5(8H, m), 1.65(2H, quint., J=6.9 Hz), 3.20(2H, q, J=6.6 Hz), 4.32(1H, brs), 4.46(2H, s), 6.57(2H, d, J=8.6 Hz), 7.31(1H, d, J=5.0 Hz), 7.55(1H, ddd, J=1.3, 6.9, 8.2 Hz), 7.71(1H, ddd, J=1.3, 6.9, 8.2 Hz), 7.90(2H, d, J=8.9 Hz), 8.06(1H, d, J=8.6 Hz), 8.18(1H, d, J=8.3 Hz), 8.72(1H, d, J=5.0 Hz)

4-[2-[4-[2-(N-Isobutyl-N-methylamino)acetylamino]-phenyl]ethylthio]quinoline (Compound 70)

MS m/z: 407 (M+); NMR(CDCl$_3$) δ: 0.97(6H, d, J=6.6 Hz), 2.25(2H, d, J=7.3 Hz), 2.34(3H, s), 3.10(2H, m), 3.11(2H, s), 3.34(2H, m), 7.21(1H, d, J=4.6 Hz), 7.55(3H, m), 8.06(1H, m), 8.13(1H, m), 8.72(1H, d, J=4.9 Hz), 9.26(1H, bs)

4-[2-[4-(3-Isobutyl-5-oxo-1-imidazolidinyl)phenyl]-2-oxoethylthio]quinoline (Compound 71)

MS m/z: 419 (M$^+$); NMR(CDCl$_3$) δ: 0.95(6H, d, J=6.6 Hz), 1.75(1H, m), 2.45(2H, d, J=7.3 Hz), 3.47(2H, s), 4.52(2H, s), 4.58(2H, s), 7.30(1H, d, J=4.6 Hz), 7.56(1H, m), 7.72(3H, m), 8.06(3H, m), 8.16(1H, m), 8.72(1H, d, J=4.9 Hz)

4-[2-[4-[N-[2-(N-Isobutyl-N-methylamino)ethyl]-N-methylamino]phenyl]ethylthio]quinoline (Compound 72)

MS m/z: 407 (M$^+$); NMR(CDCl$_3$)δ: 0.90(6H, d, J=6.6 Hz), 1.75(1H, m), 2.14(2H, m), 2.27(3H, s), 2.52(2H, m), 2.95(3H, m), 3.00(2H, m), 3.31(2H, m), 3.44(2H, m), 6.69(2H, d, J=2.0 Hz), 7.14(2H, d, J=2.0 Hz), 7.21(1H, d, J=4.9 Hz), 7.55(1H, m), 7.71(1H, m), 8.09(1H, m), 8.15(1H, m), 8.70(1H, d, J=4.6 Hz)

4-[2-[4-(1-Pivaloyl-1,2,5,6-tetrahydropyrid-4-yl)phenyl]-2-oxoethylthio]quinoline (Compound 74)

MS m/z: 444 (M$^+$); NMR(CDCl$_3$)δ: 1.33(9H, s), 2.60(2H, brs), 3.86(2H, t, J=5.6 Hz), 4.29–4.33(2H, m), 4.53(2H, s), 6.27(1H, t, J=3.6 Hz), 7.31(1H, d, J=4.8 Hz), 7.51(2H, d, J=8.6 Hz), 7.56(1H, dd, J=6.9, 8.3 Hz), 7.73(1H, dd, J=6.9, 8.3 Hz), 8.01(2H, d, J=8.6 Hz), 8.08(1H, d, J=8.3 Hz), 8.16(1H, d, J=8.3 Hz), 8.73(1H, d, J=4.8 Hz)

4-[2-[4-(1-tert-Butoxycarbonyl-4-piperidinyl)phenyl]-2-oxoethylthio]quinoline (Compound 75)

MS m/z: 462 (M$^+$); NMR(CDCl$_3$)δ: 1.49(9H, s), 1.56–1.72(2H, m), 1.84(2H, brd, J=12.5 Hz), 2.68–2.87(3H, m), 4.27(2H, brd, J=11.2 Hz), 4.53(2H, s), 7.30(1H, d, J=4.8 Hz), 7.34(2H, d, J=8.4 Hz), 7.56(1H, dd, J=6.9, 8.5 Hz), 7.72(1H, dd, J=6.9, 8.5 Hz), 7.99(2H, d, J=8.4 Hz), 8.07(1H, d, J=8.5 Hz), 8.16(1H, d, J=8.5 Hz), 8.72(1H, d, J=4.8 Hz)

Example 2
4-(4-Dimethylaminobenzylthio)-7-methylthioquinoline (Compound 31)

Thionyl chloride (2.28 ml, 31.3 mmol) was added at 0° C. to 4-dimethylaminobenzyl alcohol (4.36 g, 28.9 mmol) dissolved in methylene chloride (70 ml) and stirred still at 0° C. for one hour. The solvent was removed under reduced pressure. The residue was suspended in dry acetone (150 ml). 7-Methylthioquinoline-4(1H)-thione (4.98 g, 24.0 mmol) was added to the suspension and stirred at room temperature overnight. The reaction mixture was made basic with 2N aqueous solution of sodium hydroxide and extracted with chloroform three times. The combined chloroform layers were washed with saturated saline solution, and dried over magnesium sulfate. The solvent was removed under reduced pressure and the residue was recrystallized from ethyl acetate to obtain 4.19 g of the titled compound (51%) as white crystal.

Melting Point: 168.0–170.0° C.; MS m/z: 340 (M$^+$); NMR(CDCl$_3$) δ: 2.61(3H, s), 2.95(6H, s), 4.30(2H, s), 6.70(2H, d, J=8.6 Hz), 7.15–7.4(4H, m), 7.85(1H, s), 7.97(1H, d, J=8.9 Hz), 8.59(1H, d, J=4.9 Hz)

In accordance with the procedure of the Example 2, the following compounds were obtained from corresponding starting materials.

4-[1-[4-(2,2,2-Trichloroethoxy)carbonylaminophenyl]-ethylthio]-7-methylthioquinoline (Compound 32)

MS m/z: 501 (M$^+$); NMR(CDCl$_3$) δ: 1.75(3H, d, J=7.0 Hz), 2.59(3H, s), 4.63(1H, q, J=7.0 Hz), 4.82(2H, s), 6.95(1H, brd), 7.08(1H, d, J=5.0 Hz), 7.37(1H, d, J=2.0 Hz), 7.39–7.43(4H, m), 7.73(1H, d, J=2.0 Hz), 8.05(1H, d, J=8.9 Hz), 8.56(1H, d, J=5.0 Hz)

4-[1-(4-Dimethylaminophenyl)ethylthio]-7-methylthioquinoline (Compound 33)

MS m/z: 354 (M$^+$); NMR(CDCl$_3$) δ: 1.74(3H, d, J=6.9 Hz), 2.59(3H, s), 2.93(6H, s), 4.62(1H, q, J=6.9 Hz), 6.68(2H, d, J=8.9 Hz), 7.15(1H, d, J=5.0 Hz), 7.31(1H, d, J=8.9 Hz), 7.37(1H, dd, J=2.0, 8.9 Hz), 7.73(1H, d, J=2.0 Hz), 8.05(1H, d, J=8.9 Hz), 8.57(1H, d, J=5.0 Hz)

4-(4-Aminobenzylthio)-7-methylthioquinoline (Compound 34) MS m/z: 312 (M$^+$); NMR(CDCl$_3$) δ: 2.60(3H, s), 4.26(2H, s), 6.66(2H, d, J=8.6 Hz), 7.15–7.25(3H, m), 7.39(1H, dd, J=2.3, 8.9 Hz), 7.82(1H, d, J=2.3 Hz), 7.97(1H, d, J=8.9 Hz), 8.60(1H, d, J=4.9 Hz)

4-(4-Isobutylaminobenzylthio)-7-methoxyquinoline (Compound 35)

MS m/z: 352 (M$^+$); NMR(CDCl$_3$) δ: 0.98(6H, d, J=6.6 Hz), 1.88(1H, m), 2.93(2H, d, J=6.9 Hz), 3.95(3H, s), 4.25(2H, s), 6.56(2H, d, J=8.2 Hz), 7.13–7.25(4H, m), 7.45(1H, m), 8.00(1H, d, J=9.2 Hz), 8.60(1H, d, J=4.9 Hz)

4-(4-Ethylaminobenzylthio)-7-methylthioquinoline (Compound 36)

MS m/z: 340 (M$^+$); NMR(CDCl$_3$) δ: 1.26(3H, t, J=7.3 Hz), 2.60(3H, s), 3.15(2H, q, J=7.3 Hz), 4.25(2H, s), 6.57(2H, d, J=8.6 Hz), 7.18(1H, d, J=4.9 Hz), 7.23(2H, d, J=8.6 Hz), 7.38(1H, dd, J=2.0, 8.9 Hz), 7.80(1H, d, J=1.7 Hz), 7.98(1H, d, J=8.6 Hz), 8.60(1H, d, J=4.9 Hz)

4-[4-(3,5,5-Trimethylhexylamino)benzylthio]-7-methylthioquinoline (Compound 37)

FAB-MS m/z: 438 [M+H]$^+$; NMR(CDCl$_3$) δ: 0.90(9H, s), 0.97(3H, d, J=6.6 Hz), 1.05–1.65(5H, m), 2.59(3H, s), 3.09(2H, m), 4.23(2H, s), 6.57(2H, d, J=8.6 Hz), 7.15(1H, d, J=5.0 Hz), 7.25(2H, d, J=8.6 Hz), 7.36(1H, dd, J=2.0, 8.9 Hz), 7.74(1H, d, J=2.0 Hz), 7.97(1H, d, J=8.9 Hz), 8.61(1H, d, J=5.0 Hz)

4-[4-(2-β-Naphtyl-2-oxoethylamino)benzylthio]-7-methylthioquinoline (Compound 38)

MS m/z: 478 (M$^+$-2); NMR(CDCl$_3$) δ: 2.59(3H, s), 4.27(2H, s), 4.76(2H, d, J=4.0 Hz), 5.10(1H, bs), 6.74(2H, d, J=8.6 Hz), 7.16(1H, d, J=5.0 Hz), 7.30(2H, d, J=8.6 Hz), 7.37(1H, dd, J=2.0, 8.9 Hz), 7.63(2H, m), 7.75(1H, d, J=2.0 Hz), 7.90–8.10(5H, m), 8.55(1H, s), 8.63(1H, d, J=4.6 Hz)

4-(3-Methyl-4-methylaminobenzylthio)-7-methylthioquinoline (Compound 39)

MS m/z: 340 (M$^+$); NMR(CDCl$_3$) δ: 2.13(3H, s), 2.60(3H, s), 2.90(3H, s), 4.26(2H, s), 6.57(1H, d, J=8.3 Hz), 7.10–7.40(4H, m), 7.82(1H, bs), 7.97(1H, d, J=8.9 Hz), 8.60(1H, d, J=4.9 Hz)

4-(3-Methyl-4-dimethylaminobenzylthio)-7-methylthioquinoline (Compound 40)

MS m/z: 354 (M$^+$); NMR(CDCl$_3$) δ: 2.32(3H, s), 2.61(3H, s), 2.70(6H, s), 4.28(2H, s), 6.99(1H, d, J=8.6 Hz), 7.20(3H, m), 7.40(1H, dd, J=2.0, 8.9 Hz), 7.85(1H, s), 7.98(1H, d, J=8.9 Hz), 8.60(1H, d, J=4.9 Hz)

4-[3,4-Bis(dimethylamino)benzylthio]-7-methylthioquinoline (Compound 41)

MS m/z: 383 (M$^+$); NMR(CDCl$_3$) δ: 2.60(3H, s), 2.77(6H, s), 2.78(6H, s), 4.25(2H, s), 6.80–7.00(3H, m), 7.18(1H, d, J=4.9 Hz), 7.36(1H, dd, J=2.0, 8.6 Hz), 7.74(1H, d, J=2.0 Hz), 7.98(1H, d, J=8.9 Hz), 8.63(1H, d, J=4.9 Hz)

4-(4-Dimethylaminobenzylthio)-7-dimethylaminoquinoline (Compound 42)

MS m/z: 337 (M$^+$); NMR(CDCl$_3$) δ: 2.96(6H, s), 3.13(6H, s), 4.29(2H, s), 6.70(2H, d, J=8.9 Hz), 7.02(1H, d, J=5.3 Hz), 7.14(1H, dd, J=2.6, 9.2 Hz), 7.23–7.31(3H, m), 7.95(1H, d, J=9.6 Hz), 8.45(1H, d, J=5.3 Hz)

4-(4-Morpholinobenzylthio)-7-methylthioquinoline (Compound 43)

MS m/z: 382 (M$^+$); NMR(CDCl$_3$) δ: 2.60(3H, s), 3.16(4H, m), 3.85(4H, m), 4.27(2H, s), 6.87(2H, d, J=8.9 Hz), 7.14(1H, d, J=4.9 Hz), 7.33(2H, d, J=8.9 Hz), 7.37(1H, dd, J=2.3, 8.9 Hz), 7.74(1H, d, J=2.0 Hz), 7.97(1H, d, J=8.9 Hz), 8.61(1H, d, J=4.9 Hz)

4-[4-(1-Pyrrolidinyl)benzylthio]-7-methylthioquinoline (Compound 44)

MS m/z: 366 (M$^+$); NMR(CDCl$_3$) δ: 2.00(4H, m), 2.61 (3H, s), 3.28(4H, m), 6.53(2H, d, J=8.6 Hz), 7.21(1H, d, J=4.9 Hz), 7.29(2H, d, J=8.6 Hz), 7.38(1H, dd, J=2.0, 8.9 Hz), 7.84(1H, s), 7.98(1H, d, J=8.9 Hz), 8.59(1H, d, J=4.9 Hz)

4-(4-Piperidinobenzylthio)-7-methylthioquinoline (Compound 45)

MS m/z: 380 (M$^+$); NMR(CDCl$_3$) δ: 1.50–1.80(6H, m), 2.60(3H, s), 3.16(4H, m), 4.25(2H, s), 6.89(2H, d, J=8.9 Hz), 7.15(1H, d, J=4.9 Hz), 7.29(2H, d, J=8.9 Hz), 7.36(1H, dd, J=2.0, 8.9 Hz), 7.74(1H, d, J=2.0 Hz), 7.97(1H, d, J=8.9 Hz), 8.61(1H, d, J=4.9 Hz)

4-[4-(4-Methyl-1-piperazinyl)benzylthio]-7-methylthioquinoline (Compound 46)

MS m/z: 395 (M$^+$); NMR(CDCl$_3$) δ: 2.35(3H, s), 2.57 (4H, m), 2.59(3H, s), 3.22(4H, m), 4.26(2H, s), 6.89(2H, d, J=8.6 Hz), 7.14(1H, d, J=4.9 Hz), 7.32(2H, d, J=8.6 Hz), 7.37(1H, dd, J=2.0, 8.9 Hz), 7.74(1H, d, J=2.0 Hz), 7.97(1H, d, J=8.9 Hz), 8.61(1H, d, J=4.9 Hz)

4-[4-[Bis(2-acetoxyethyl)amino]benzylthio]-7-methylthioquinoline (Compound 47)

MS m/z: 484 (M$^+$); NMR(CDCl$_3$) δ: 2.04(6H, s), 2.60 (3H, s), 3.60(4H, m), 4.24(6H, m), 6.72(2H, d, J=8.9 Hz), 7.16(1H, d, J=4.9 Hz), 7.29(2H, d, J=8.9 Hz), 7.37(1H, dd, J=2.0, 8.9 Hz), 7.74(1H, d, J=2.0 Hz), 7.96(1H, d, J=8.9 Hz), 8.62(1H, d, J=4.9 Hz)

4-[4-[N-(2-Acetoxyethyl)-2-hydroxyethylamino] benzylthio]-7-methylthioquinoline (Compound 48)

MS m/z: 442 (M$^+$); NMR(CDCl$_3$) δ: 2.02(3H, s), 2.60 (3H, s), 3.53(2H, m), 3.64(2H, m), 3.80(2H, m), 4.24(4H, m), 6.75(2H, d, J=8.9 Hz), 7.16(1H, d, J=5.0 Hz), 7.28(2H, d, J=8.9 Hz), 7.37(1H, dd, J=2.3, 8.9 Hz), 7.74(1H, d, J=2.3 Hz), 7.97(1H, d, J=8.9 Hz), 8.62(1H, d, J=5.0 Hz)

4-[4-(4-Formyl-1-piperazinyl)benzylthio]-7-methylthioquinoline (Compound 63)

MS m/z: 409 (M$^+$); NMR(CDCl$_3$) δ: 2.60(3H, s), 3.18 (4H, m), 3.52(2H, m), 3.70(2H, m), 4.26(2H, s), 6.90(2H, d, J=8.6 Hz), 7.14(1H, d, J=5.0 Hz), 7.34(2H, d, J=8.6 Hz), 7.37(1H, m), 7.74(1H, d, J=2.0 Hz), 7.97(1H, d, J=8.9 Hz), 8.11(1H, s), 8.61(1H, d, J=5.0 Hz)

Example 3

4-[2-[4-(4-tert-Butoxycarbonyl-1-piperazinyl)phenyl]-2-oxoethylthio]quinoline (Compound 49)

Quinoline-4(1H)-thione (2.00 g, 12.2 mmol) and potassium carbonate (5.40 g, 39.0 mmol) were suspended in dry acetone (400 ml). 1-Bromoacetyl-4-(1-piperazinyl)-benzene dihydrobromide (5.64 g, 12.2 mmol) was gradually added under ice cooling to the suspension and stirred at room temperature overnight. The solvent was removed under reduced pressure. The residue was added with ethanol (400 ml) and then added with di-tert-butyl dicarbonate (8.70 g). The reaction mixture was further stirred at room temperature overnight and the solvent was removed under reduced pressure. The residue was added with water, extracted with ethyl acetate, washed with saturated saline solution and dried over anhydrous magnesium sulfate. The solvent was removed under reduced pressure. The residue was chromatographed by silica gel column chromatography (n-hexane:ethyl acetate=1:4) to obtain 3.58 g of the titled compound (63.3%).

Melting Point: 153.0–154.5° C.; MS m/z: 463 (M$^+$); NMR(CDCl$_3$) δ: 1.49(9H, s), 3.39(4H, brt, J=5.3 Hz), 3.59(4H, brt, J=5.3 Hz), 4.48(2H, s), 6.88(2H, d, J=9.2 Hz), 7.32(1H, d, J=5.0 Hz), 7.55(1H, ddd, J=1.3, 6.9, 8.2 Hz), 7.72(1H, ddd, J=1.2, 6,9, 8.3 Hz), 7.96(2H, d, J=8.9 Hz), 8.07(1H, brd, J=8.6 Hz), 8.17(1H, dd, J=1.0, 8.3 Hz), 8.71(1H, d, J=5.0 Hz)

In accordance with the procedure of the Example 3, the following compounds were obtained from corresponding starting materials.

4-[2-[4-[2-(4-tert-Butoxycarbonyl-1-piperazinyl)ethyl]-phenyl]-2-oxoethylthio]quinoline (Compound 50)

MS m/z: 491 (M$^+$); NMR(CDCl$_3$) δ: 1.28(9H, s), 2.52 (4H, brs), 2.68(2H, brt, J=8.3 Hz), 2.93(2H, brt, J=8.3 Hz), 3.50(4H, brs), 4.53(2H, s), 7.30(1H, d, J=5.0 Hz), 7.35(2H, d, J=8.3 Hz), 7.56(1H, ddd, J=1.3, 6.9, 8.2 Hz), 7.72(1H, ddd, J=1.3, 6.9, 8.3 Hz), 7.97(2H, d, J=8.3 Hz), 8.07(1H, d, J=7.9 Hz), 8.16(1H, d, J=8.2 Hz), 8.72(1H, d, J=4.6 Hz)

4-[2-[4-(4-tert-Butoxycarbonyl-1-homopiperazinyl) phenyl]-2-oxoethylthio]quinoline (Compound 76)

MS m/z: 477 (M$^+$); NMR(CDCl$_3$) δ: 1.35(9H, s), 1.95–2.05(2H, m), 3.2–3.4(2H, m), 3.55–3.70(6H, m), 4.45 (2H, s), 6.71(2H, d, J=8.9 Hz), 7.32(1H, d, J=5.4 Hz), 7.55(1H, t, J=7.6 Hz), 7.71(1H, ddd, J=1.0, 6.9, 7.9 Hz), 7.93(2H, d, J=8.9 Hz), 8.06(1H, d, J=8.6 Hz), 8.17(1H, d, J=8.3 Hz), 8.71(1H, d, J =4.6 Hz)

4-[2-[4-(4-tert-Butoxycarbonyl-1-piperazinyl)phenyl]-2-oxoethylthio]-6-fluoroquinoline (Compound 73)

MS m/z: 481 (M$^+$); NMR(CDCl$_3$) δ: 1.48(9H, s), 3.38 (4H, m), 3.59(4H, m), 4.46(2H, s), 6.88(2H, d, J=8.9 Hz), 7.34(1H, d, J=4.6 Hz), 7.47(1H, m), 7.79(1H, m), 7.95(2H, d, J=8.9 Hz), 8.06(1H, m), 8.67(1H, d, J=4.9 Hz)

Example 4

4-[2-[4-(1-Piperazinyl)phenyl]-2-oxoethylthio]quinoline hydrochloride (Compound 51)

4-[2-[4-(4-tert-Butoxycarbonyl-1-piperazinyl)phenyl]-2-oxoethylthio]quinoline (Compound 49; 2.8 g, 6.0 mmol) was gradually added to an ice-cooled solution of 4N hydrochloride dioxane solution (40 ml). The reaction mixture was stirred at room temperature for one hour. The resulting precipitates were collected by filtration and washed well with dry dioxane and dry ether to obtain 2.8 g of the titled compound (99%).

Melting Point: 217.5° C. (decomp.); FAB-MS m/z: 364 [M+H]$^+$; NMR(DMSO-d$_6$) δ: 3.30(4H, brt, J=5.3 Hz), 3.60 (4H, brt, J=5.3 Hz), 5.09(2H, s), 7.06(2H, d, J=9.2 Hz), 7.80(1H, d, J=6.3 Hz), 7.88(1H, m), 8.02(2H, d, J=9.2 Hz), 8.05–8.10(2H, m), 8.46(1H, brd, J=8.2 Hz), 8.47(1H, d, J=6.3 Hz)

Example 5

4-[2-[4-(4-Pivaloyl-1-piperazinyl)phenyl]-2-oxoethylthio] quinoline (Compound 52)

4-[2-[4-(1-Piperazinyl)phenyl]-2-oxoethylthio]-quinoline hydrochloride (Compound 51; 2.20 g, 4.66 mmol) was suspended in dry acetone (300 ml). Triethylamine (6.60 ml, 47.2 mmol) was added at −15° C. to the suspension and, after 30 minutes, pivaloylchloride (1.25 ml, 10.0 mmol) was added dropwise to the suspension. The reaction mixture was stirred at room temperature overnight and the solvent was removed under reduced pressure. The residue was chromatographed by silica gel chromatography (dichloromethane:methanol=20:1) to obtain 1.50 g of the titled compound (72.0%).

Melting Point: 174.5–175.5° C.; MS m/z: 447 (M$^+$); NMR(CDCl$_3$) δ: 1.32(9H, s), 3.41(4H, t, J=5.0 Hz), 3.83 (4H, t, J=5.0 Hz), 4.53(2H, s), 6.90(2H, d, J=9.2 Hz), 7.37(1H, d, J=5.0 Hz), 7.61(1H, brt, J=7.9 Hz), 7.78(1H, brt, J=7.9 Hz), 7.97(2H, d, J=8.9 Hz), 8.15–8.25(2H, m), 8.72 (1H, d, J=5.0 Hz)

In accordance with the procedure of the Example 5, the following compounds were obtained from corresponding starting materials.

4-[2-[4-[4-(4-Methoxycinnamoyl)-1-piperazinyl]phenyl]-2-oxoethylthio]quinoline (Compound 53)

MS m/z: 523 (M$^+$); NMR(CDCl$_3$) δ: 3.48(4H, brt, J=5.2 Hz), 3.84(3H, s), 3.88(4H, brs), 4.48(2H, s), 6.76(1H, d, J=15.2 Hz), 6.90(2H, d, J=8.9 Hz), 6.91(2H, d, J=8.9 Hz), 7.32(1H, d, J=4.9 Hz), 7.49(2H, d, J=8.9 Hz), 7.55(1H, ddd, J=1.0, 6.9, 8.3 Hz), 7.70(1H, d, J=15.5 Hz), 7.72(1H, ddd, J=1.3, 6.9, 8.3 Hz), 7.98(2H, d, J=8.9 Hz), 8.07(1H, brd, J=7.9 Hz), 8.17(1H, brd, J=8.2 Hz), 8.71(1H, d, J=5.0 Hz)

4-[2-[4-(4-Diethylaminothiocarbonyl-1-piperazinyl)phenyl]-2-oxoethylthio]quinoline (Compound 54)

MS m/z: 478 (M$^+$); NMR(CDCl$_3$) δ: 1.24(6H, t, J=6.9 Hz), 3.49(4H, brs), 3.61(4H, brs), 3.66(4H, q, J=7.3 Hz), 4.49(2H, s), 6.68(2H, d, J=8.9 Hz), 7.32(1H, d, J=5.0 Hz), 7.55(1H, ddd, J=1.3, 6.9, 8.2 Hz), 7.72(1H, ddd, J=1.3, 6.9, 8.3 Hz), 7.96(2H, d, J=8.9 Hz), 8.08(1H, d, J=8.3 Hz), 8.17(1H, d, J=8.6 Hz), 8.71(1H, d, J=5.0 Hz)

4-[2-[4-(4-Benzyloxycarbonyl-1-piperazinyl)phenyl)-2-oxoethylthio]quinoline (Compound 78)

MS m/z: 497 (M$^+$); NMR(CDCl$_3$) δ: 3.40(4H, t, J=5.0 Hz), 3.68(4H, t, J=5.3 Hz), 4.47(2H, s), 5.17(2H, s), 6.88(2H, d, J=9.2 Hz), 7.31(1H, d, J=4.6 Hz), 7.37(5H, s), 7.55(1H, ddd, J=1.0, 6.9, 8.2 Hz), 7.71(1H, ddd, J=1.3, 6.9, 8.3 Hz), 7.96(2H, d, J=9.2 Hz), 8.06(1H, d, J=8.6 Hz), 8.17(1H, dd, J=1.0, 8.3 Hz), 8.71(1H, d, J=5.0 Hz)

4-[2-[4-[4-(N-tert-Butoxycarbonylvalyl)-1-piperazinyl]phenyl]-2-oxoethylthio]quinoline (Compound 79) MS m/z: 562 (M$^+$);

NMR(CDCl$_3$) δ: 0.95(6H, dd, J=6.6, 15.5 Hz), 1.44(9H, s), 1.96(1H, m), 3.4–3.5(4H, m), 3.6–4.0(4H, m), 4.48(3H, m), 5.28(1H, d, J=8.9 Hz), 6.89(2H, d, J=8.9 Hz), 7.31(1H, d, J=4.6 Hz), 7.55(1H, ddd, J=1.3, 6.9, 8.2 Hz), 7.72(1H, ddd, J=1.3, 6.9, 8.3 Hz), 7.97(2H, d, J=8.9 Hz), 8.07(1H, dd, J=0.7, 8.6 Hz), 8.17(1H, dd, J=1.0, 8.6 Hz), 8.71(1H, d, J=4.6 Hz)

4-[2-[4-(4-Phenoxycarbonyl-1-piperazinyl)phenyl]-2-oxoethylthio]quinoline (Compound 80)

MS m/z: 483 (M$^+$); NMR(CDCl$_3$) δ: 3.50(4H, brt, J=5.3 Hz), 3.80(4H, brs), 4.49(2H, s), 6.93(2H, d, J=8.9 Hz), 7.13(2H, brd, J=7.6 Hz), 7.25(1H, brt, J=7.6 Hz), 7.33(1H, d, J=5.0 Hz), 7.38(2H, t, J=7.6 Hz), 7.56(1H, ddd, J=1.3, 6.9, 8.2 Hz), 7.72(1H, ddd, J=1.3, 6.9, 8.3 Hz), 7.99(2H, d, J=8.9 Hz), 8.07(1H, d, J=7.9 Hz), 8.17(1H, dd, J=1.0, 8.6 Hz), 8.72(1H, d, J=5.0 Hz)

4-[2-[4-[4-(2,2,2-Trichloroethoxycarbonyl)-1-piperazinyl]phenyl]-2-oxoethylthio]quinoline (Compound 81)

MS m/z:537 (M$^+$); NMR(CDCl$_3$) δ: 3.45(4H, brt, J=5.3 Hz), 3.75(4H, brs), 4.48(2H, s), 4.80(2H, s), 6.90(2H, d, J=9.2 Hz), 7.32(1H, d, J=5.0 Hz), 7.55(1H, ddd, J=1.3, 6.9, 8.2 Hz), 7.72(1H, ddd, J=1.3, 6.9, 8.6 Hz), 7.97(2H, d, J=8.9 Hz), 8.07(1H, d, J=8.3 Hz), 8.17(1H, d, J=9.2 Hz), 8.72(1H, d, J=4.6 Hz)

4-[2-[4-(4-Ethoxycarbonyl-1-piperazinyl)phenyl]-2-oxoethylthio]quinoline (Compound 82)

MS m/z: 435 (M$^+$); NMR(CDCl$_3$) δ: 1.29(3H, t, J=7.1 Hz), 3.40(4H, t, J=5.3 Hz), 3.65(4H, t, J=5.3 Hz), 4.19(2H, q, J=7.3 Hz), 4.48(2H, s), 6.89(2H, d, J=8.9 Hz), 7.32(1H, d, J=5.0 Hz), 7.55(1H, ddd, J=1.3, 6.9, 8.2 Hz), 7.72(1H, ddd, J=1.3, 6.9, 8.2 Hz), 7.96(2H, d, J=9.2 Hz), 8.07(1H, d, J=8.3 Hz), 8.17(1H, dd, J=1.0, 8.6 Hz), 8.72(1H, d, J=5.0 Hz)

4-[2-[4-(4-Allyloxycarbonyl-1-piperazinyl)phenyl]-2-oxoethylthio]quinoline (Compound 83)

MS m/z: 447 (M$^+$); NMR(CDCl$_3$) δ: 3.41(4H, t, J=5.3 Hz), 3.67(4H, t, J=5.3 Hz), 4.47(2H, s), 4.64(2H, dt, J=1.3, 5.6 Hz), 5.24(1H, dd, J=1.3, 10.2 Hz), 5.32(1H, dd, J=1.3, 17.2 Hz), 5.90–6.05(1H, m), 6.89(2H, d, J=9.2 Hz), 7.31 (1H, d, J=4.6 Hz), 7.55(1H, ddd, J=1.3, 6.9, 8.2 Hz), 7.72(1H, ddd, J=1.3, 6.9, 8.3 Hz), 7.97(2H, d, J=8.9 Hz), 8.06(1H, d, J=8.6 Hz), 8.17(1H, d, J=7.9 Hz), 8.71(1H, d, J=5.0 Hz)

4-[2-(4-(4-Dimethylsulfamoyl-1-piperazinyl)phenyl]-2-oxoethylthio]quinoline (Compound 84)

MS m/z: 470 (M$^+$); NMR(CDCl$_3$) δ: 2.87(6H, s), 3.35–3.50(8H, m), 4.48(2H, s), 6.91(2H, d, J=8.9 Hz), 7.31(1H, d, J=5.0 Hz), 7.55(1H, ddd, J=1.3, 6.9, 8.2 Hz), 7.72(1H, ddd, J=1.3, 6.9, 8.6 Hz), 7.97(2H, d, J=9.2 Hz), 8.07(1H, d, J=7.9 Hz), 8.17(1H, dd, J=1.0, 8.6 Hz), 8.71(1H, d, J=5.0 Hz)

4-[2-[4-[4-(N-tert-Butylcarbamoyl)-1-piperazinyl]phenyl]-2-oxoethylthio]quinoline (Compound 85)

MS m/z: 462 (M$^+$); NMR(CDCl$_3$) δ: 1.38(9H, s), 3.40–3.56(8H, m), 4.47(2H, s), 6.86(2H, d, J=8.9 Hz), 7.30(1H, d, J=4.6 Hz), 7.55(1H, ddd, J=1.3, 6.9, 8.3 Hz), 7.72(1H, ddd, J=1.3, 6.9, 8.3 Hz), 7.96(2H, d, J=8.9 Hz), 8.07(1H, d, J=8.3 Hz), 8.17(1H, dd, J=1.0, 8.3 Hz), 8.71(1H, d, J=4.6 Hz)

4-[2-[4-(4-Methanesulfonyl-1-piperazinyl)phenyl]-2-oxoethylthio]quinoline (Compound 86)

MS m/z:441 (M$^+$); NMR(CDCl$_3$) δ: 2.83(3H, s), 3.39(4H, t, J=5.0 Hz), 3.51(4H, t, J=5.3 Hz), 4.47(2H, s), 6.92(2H, d, J=8.9 Hz), 7.31(1H, d, J=4.6 Hz), 7.55(1H, ddd, J=1.3, 6.9, 8.2 Hz), 7.72(1H, ddd, J=1.3, 6.9, 8.3 Hz), 7.97(2H, d, J=8.9 Hz), 8.07(1H, d, J=8.3 Hz), 8.16(1H, dd, J=1.0, 8.6 Hz), 8.71(1H, d, J=4.6 Hz)

Example 6

4-[2-[2-Methoxy-4-hexyloxyphenyl]-2-oxoethylthio]-quinoline (Compound 55)

4-[2-(4-Hydroxy-2-methoxyphenyl)-2-oxoethylthio]-quinoline (Compound 12; 83 mg, 0.25 mmol) and potassium carbonate(42 mg, 0.25 mmol) were suspended in dry DMF (2.0 ml). Hexylbromide (0.041 ml, 0.28 mmol) was addded at −15° C. to the suspension and stirred at room temperature overnight. The reaction mixture was added with water under ice cooling, extracted with ethyl acetate, washed with saturated saline solution and dried over anhydrous magnesium sulfate. The solvent was removed under reduced pressure. The residue was chromatographed by silica gel chromatography (n-hexane:ethyl acetate=1:4) to obtain 82.1 mg of the titled compound (80.3%).

Melting Point: 88.5–89.5° C.; MS m/z: 409 (M$^+$); NMR (CDCl$_3$) δ: 0.91(3H, t, J=6.9 Hz), 1.3–1.55(6H, m), 1.80(2H, quint, J=6.9 Hz), 3.99(3H, s), 4.02(2H, t, J=6.6 Hz), 4.58 (2H, s), 6.50(1H, d, J=2.3 Hz), 6.56(1H, dd, J=2.1, 8.9 Hz), 7.33(1H, d, J=5.0 Hz), 7.58(1H, brt, J=7.6 Hz), 7.75(1H, brt, J=7.6 Hz), 7.91(1H, d, J=8.6 Hz), 8.20(2H, m), 8.68(1H, d, J=5.3 Hz)

In accordance with the procedure of the Example 6, the following compounds were obtained from corresponding starting materials.

4-[2-[4-(4-Methoxybenzyloxy)phenyl]-2-oxoethylthio]-quinoline (Compound 56)

MS m/z: 415 (M$^+$); NMR(CDCl$_3$) δ: 3.83(3H, s), 4.50 (2H, s), 5.08(2H, s), 6.93(2H, d, J=8.9 Hz), 7.04(2H, d, J=8.9 Hz), 7.30(1H, d, J=5.0 Hz), 7.36(2H, d, J=8.6 Hz), 7.56(1H, ddd, J=1.3, 6.9, 8.2 Hz), 7.72(1H, ddd, J=1.3, 6.9, 8.3 Hz), 8.02(2H, d, J=8.9 Hz), 8.07(1H, brd, J=8.9 Hz), 8.17(1H, dd, J=0.8, 8.6 Hz), 8.72(1H, d, J=5.0 Hz)

4-[2-[3-Methoxy-4-(2,3-epoxypropoxy)phenyl]-2-oxoethylthio]quinoline (Compound 57)

MS m/z: 381 (M$^+$); NMR(CDCl$_3$) δ: 2.79(1H, dd, J=2.6, 5.0 Hz), 2.94(1H, t, J=4.6 Hz), 3.41(1H, m), 3.93(3H, s), 4.11(1H, dd, J=5.6, 11.6 Hz), 4.40(1H, dd, J=3.0, 11.6 Hz), 4.53(2H, s), 7.00(1H, d, J=8.3 Hz), 7.34(1H, d, J=5.0 Hz), 7.55–7.62(2H, m), 7.65(1H, dd, J=2.2, 8.3 Hz), 7.75(1H, ddd, J=1.3, 6.9, 8.3 Hz), 8.17(2H, brt, J=8.9 Hz), 8.72(1H, d, J=5.0 Hz)

4-[2-[3-Methoxy-4-(4-methoxybenzyloxy)phenyl]-2-oxoethylthio]quinoline (Compound 58)

MS m/z: 445 (M$^+$); NMR(CDCl$_3$) δ: 3.81(3H, s), 3.93(3H, s), 4.52(2H, s), 5.18(2H, s), 6.91(2H, d, J=8.6 Hz), 6.96(1H, d, J=8.6 Hz), 7.34(1H, d, J=5.0 Hz), 7.37(2H, d, J=8.9 Hz), 5.57(1H, d, J=2.0 Hz), 7.61(2H, d, J=8.2 Hz), 7.76(1H, brt, J=7.0 Hz), 8.19(2H, m), 8.71(1H, d, J=5.0 Hz)

4-[2-[4-(5-Ethoxycarbonyl-n-pentyloxy)phenyl]-2-oxoethylthio]quinoline (Compound 59)

MS m/z: 437 (M$^+$); NMR(CDCl$_3$) δ: 1.26(3H, t, J=7.3 Hz), 1.5–1.9(6H, m), 2.34(2H, t, J=7.3 Hz), 4.05(2H, t, J=7.3 Hz), 4.13(2H, q, J=7.3 Hz), 4.50(2H, s), 6.95(2H, m), 7.30(1H, d, J=4.6 Hz), 7.56(1H, m), 7.72(1H, m), 8.07(1H, dd, J=0.7, 8.6 Hz), 8.17(1H, dd, J=1.0, 8.6 Hz), 8.72(1H, d, J=4.6 Hz)

Example 7

4-[2-[3-Methoxy-4-(2,3-dihydroxypropoxy)phenyl]-2-oxoethylthio]quinoline (Compound 60)

4-[2-[3-Methoxy-4-(2,3-epoxypropoxy)phenyl]-2-oxoethylthio]quinoline (Compound 57; 2.0 g, 5.25 mmol) was added at 0° C. to the mixture of formic acid (40 ml) and water (4 ml), and stirred at room temperature overnight. The solvent was removed under reduced pressure. The residue was added with an ice-cooled aqueous solution of 40% sodium hydroxide (7.0 ml) and stirred at 0° C. for 30 minutes. The solvent was removed under reduced pressure and the residue was chromatographed by silica gel column chromatography (dichloromethane:methanol=20:1) to obtain 1.4 g of the titled compound (67.0%). Melting Point: 177° C. (decomp.)

MS m/z: 399 (M$^+$); NMR(CD$_3$OD-CDCl$_3$) δ: 3.74(2H, dd, J=1.7, 4.6 Hz), 3.95(3H, s), 4.12(2H, br.quint, J=6.6 Hz), 4.20(1H, quint, J=6.1 Hz), 4.76(2H, s), 7.07(1H, d, J=8.6 Hz), 7.48(1H, d, J=5.3 Hz), 7.61(1H, d, J=2.0 Hz), 7.68(1H, ddd, J=1.3, 6.9, 8.2 Hz), 7.75–7.9(2H, m), 8.04(1H, brd, J=8.6 Hz), 8.27(1H, dd, J=0.7, 8.6 Hz), 8.65(1H, d, J=5.2 Hz)

Example 8

4-[2-(2-Naphtyl)-2-hydroxyethylthio]quinoline (Compound 61)

4-[2-(2-Naphtyl)-2-oxoethylthio]quinoline (Compound 2; 450 mg, 1.37 mmol) was dissolved in ethanol (50 ml), added at −15° C. with sodium borohydride (70 mg, 3.04 mmol), and stirred at −15° C. for two hours. The reaction mixture was added with water and neutralized by 2N hydrochloric acid. The solvent was removed under reduced pressure. The residue was extracted with ethyl acetate, washed with saturated saline solution and dried over anhydrous magnesium sulfate. The solvent was removed under reduced pressure and the residue was chromatographed by silica gel column chromatography (hexane:ethyl acetate=1:4) to obtain 165.7 mg of the titled compound (36.5%).

Melting Point: 170.5–172.5° C. MS m/z: 331 (M$^+$); NMR(CDCl$_3$) δ: 3.59(2H, t, J=6.9 Hz), 5.20(1H, dd, J=5.6, 6.9 Hz), 7.38(1H, d, J=5.0 Hz), 7.45–7.55(2H, m), 7.60(1H, ddd, J=1.3, 5.0, 6.9 Hz), 7.77(1H, ddd, J=1.3, 7.0, 8.3 Hz), 7.8–7.9(5H, m), 8.03(1H, d, J=8.6 Hz), 8.19(1H, brd, J=7.8 Hz), 8.60(1H, d, J=5.0 Hz), 4-[2-[4-(4-tert-Butoxycarbonyl-1-piperazinyl)phenyl]-2-hydroxyethylthio]quinoline (Compound 87)

MS m/z: 465 (M$^+$); NMR(CDCl$_3$) δ: 1.49(9H, s), 2.50 (1H, brs), 3.15(4H, t, J=5.1 Hz), 3.44(2H, brd, J=6.4 Hz), 3.58(4H, t, J=5.1 Hz), 4.94(1H, brt, J=6.3 Hz), 6.93(2H, d, J=8.6 Hz), 7.26(1H, d, J=4.6 Hz), 7.34(2H, d, J=8.6 Hz), 7.56(1H, ddd, J=1.3, 6.9, 8.2 Hz), 7.73(1H, ddd, J=1.3, 6.6, 8.3 Hz), 8.07(1H, d, J=8.3 Hz), 8.17(1H, dd, J=1.1, 8.3 Hz), 8.71(1H, d, J=5.0 Hz)

Example 9

4-[4-[Bis(2-hydroxyethyl)amino]benzylthio]-7-methylthioquinoline (Compound 62)

4-[4-[Bis(2-acetoxyethyl)amino]benzylthio]-7-methylthioquinoline (Compound 47; 30 mg, 0.06 mmol) was dissolved in methanol (5 ml) and added with potassium carbonate (34 mg, 0.247 mmol) and stirred at room temperatue for two hours. Methanol was removed under reduced pressure. The reaction mixture was added with water and extracted twice with chloroform. The combined chloroform layers were washed with saturated saline solution. The solvent was removed under reduced pressure and the residue was washed with ethyl acetate to obtain 20 mg of the titled compound (81%).

Melting Point: 162–165° C.; MS m/z: 400 (M$^+$); NMR (CDCl$_3$) δ: 2.60(3H, s), 3.60(4H, m), 3.87(4H, m), 4.25(2H, s), 6.67(2H, d, J=8.6 Hz), 7.17(1H, d, J=4.6 Hz), 7.28(2H, d, J=8.6 Hz), 7.36(1H, dd, J=2.0, 8.9 Hz), 7.74(1H, d, J=2.0 Hz), 7.96(1H, d, J=8.9 Hz), 8.62(1H, d, J=4.6 Hz)

CAPABILITY OF EXPLOITATION IN INDUSTRY

The compounds of the present invention can be applied as selective antibacterial agent against Hp for the treatment of peptic ulcer and chronic gastritis with Hp infection.

We claim:

1. A quinoline sulfide compound, represented by the formula I or pharmaceutically acceptable salts thereof:

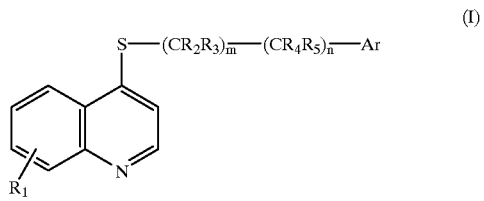

(I)

wherein R$_1$ represents hydrogen or halogen atom, C$_1$–C$_6$ alkoxy, C$_1$–C$_6$ alkylthio or di C$_1$–C$_6$ alkylamino; R$_2$ and R$_3$ respectively represent hydrogen atom or C$_1$–C$_6$ alkyl; one of R$_4$ and R$_5$ represents hydroxyl group and the other represents hydrogen atom or CR$_4$R$_5$ represents carbonyl;

m and n are integers, m being 1 or 2, n being 0 or 1;

wherein when n is 0, Ar represents a group of the formula II or III

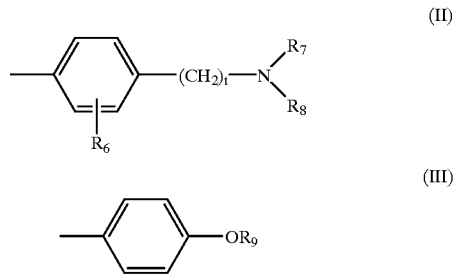

(II)

(III)

wherein R$_6$ represents hydrogen atom, C$_1$–C$_6$ alkyl or di C$_1$–C$_6$ alkylamino; R$_7$ represents hydrogen atom, C$_1$–C$_9$ alkyl, hydroxy $C_1$–$C_6$ alkyl, napthoyl $C_1$–$C_6$ alkyl, acetoxy $C_1$–$C_6$ alkyl, $C_1$–$C_6$ alkoxycarbonyl, trihalo $C_1$–$C_6$ alkoxycarbonyl, di $C_1$–$C_6$ alkylaminoacetyl or di $C_1$–$C_6$ alkylamino $C_1$–$C_6$ alkyl; $R_8$ represents hydrogen atom, $C_1$–$C_6$ alkyl, hydroxy $C_1$–$C_6$ alkyl or acetoxy $C_1$–$C_6$ alkyl, or $NR_7R_8$ represents pyrrolidinyl, piperidino, morpholino or piperazinyl (which may be substituted by $C_1$–$C_6$ alkyl or formyl); $R_9$ represents benzyl; and t is an integer and is 0 or 1;

and wherein when n is 1, Ar represents naphthyl, fluorenyl or a group of the formula IV, V or VI

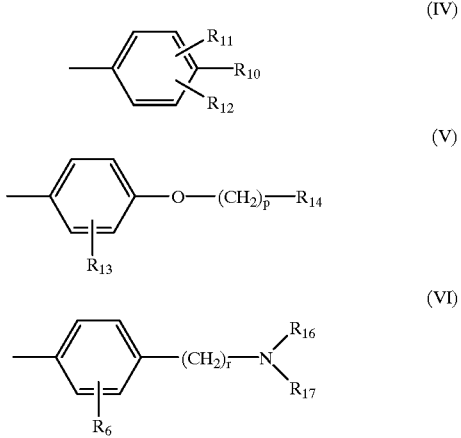

wherein $R_{10}$ represents hydrogen atom, $C_1$–$C_6$ alkyl, hydroxyl group, $C_1$–$C_6$ alkoxy, epoxy $C_1$–$C_6$ alkoxy, mono- or dihydroxy $C_1$–$C_6$ alkoxy, phenyl, piperidinyl (which may be substituted by $C_1$–$C_6$ alkylcarbonyl or $C_1$–$C_6$ alkoxycarbonyl), or tetrahydropyridyl (which may be substituted by $C_1$–$C_6$ alkylcarbonyl); $R_{11}$ represents hydrogen atom, $C_1$–$C_6$ alkoxy or benzyloxy; $R_{12}$ represents hydrogen atom or $C_1$–$C_6$ alkoxy; $R_{13}$ represents hydrogen atom or $C_1$–$C_6$ alkoxy; $R_{14}$ represents $C_1$–$C_6$ alkoxycarbonyl, phenyl (which may be substituted by $C_1$–$C_6$ alkoxy), or benzoyl (which may be substituted by $C_1$–$C_6$ alkyl); $R_{15}$ represents hydrogen or halogen atom; $R_{16}$ represents hydrogen atom, $C_1$–$C_6$ alkyl, $C_1$–$C_6$ alkylcarbonyl, $C_1$–$C_6$ alkoxycarbonyl, or pyrrolidinyl (which may be substituted by $C_1$–$C_6$ alkoxycarbonyl); $R_{17}$ represents hydrogen atom, $C_1$–$C_9$ alkyl or benzyl, or $NR_{16}R_{17}$ represents piperidino, morpholino, piperazinyl (which may be substituted by $C_1$–$C_6$ alkyl, $C_1$–$C_6$ alkylcarbonyl, $C_1$–$C_6$ alkoxycarbonyl, trihalo $C_1$–$C_6$ alkoxycarbonyl, $C_2$–$C_6$ alkenyloxycarbonyl, phenoxycarbonyl, benzyloxycarbonyl, amino $C_1$–$C_6$ alkylcarbonyl (amino group may be substituted by $C_1$–$C_6$ alkoxycarbonyl), cinnamoyl (which may be substituted by $C_1$–$C_6$ alkoxy), $C_1$–$C_6$ alkylcarbamoyl, di $C_1$–$C_6$ alkylsulfamoyl, $C_1$–$C_6$ alkylsulfonyl, di $C_1$–$C_6$ alkylaminothiocarbonyl, pyrimidyl or phenyl (which may be substituted by halogen atom)), imidazolidinyl (which may be substituted by oxo or $C_1$–$C_6$ alkyl) or homopipermzinyl (which may be substituted by $C_1$–$C_6$ alkoxycarbonyl); p is an integer within a range of 0–5 and r is an integer within a range of 0–2;

with the proviso that when m and n are both 1, $CR_4R_5$ is carbonyl, and Ar is the group of the formula IV, then $R_1$, $R_2$, $R_3$, $R_{10}$, $R_{11}$ and $R_{11}$ are not hydrogen atoms; and with the proviso that when m is 1, n is 0, and Ar is 4-aminophenyl, then $R_1$ is not hydrogen, halogen atom or $C_1$–$C_6$ alkoxy.

2. The compound according to claim 1 wherein m and n are both 1.

3. The compound according to claim 1 wherein m and n are both 1 and $CR_4R_5$ is carbonyl.

4. The compound according to claim 1 wherein m and n are both 1, $CR_4R_5$ is carbonyl, and $R_1$, $R_2$ and $R_3$ are hydrogen atoms.

5. The compound according to claim 1 wherein m and n are both 1, $CR_4R_5$ is carbonyl, $R_1$, $R_2$ and $R_3$ are hydrogen atoms, and Ar is a group of the formula VI.

6. A pharmaceutical composition, comprising the compound as claimed in claim 1 and a pharmaceutically acceptable diluent or carrier.

7. The compound according to claim 1, wherein m and n are both 1, r is 0, $CR_4R_5$ is carbonyl, $R_1$, $R_2$ and $R_3$ are hydrogen atoms, Ar is a group of the formula VI, and $NR_{16}R_{17}$ is piperazinyl which may be substituted by a substituent selected from the group consisting of $C_1$–$C_6$ alkyl, $C_1$–$C_6$ alkylcarbonyl, $C_1$–$C_6$ alkoxycarbonyl, trihalo $C_1$–$C_6$ alkoxycarbonyl, $C_2$–$C_6$ alkenyloxycarbonyl, phenoxycarbonyl, benzyloxycarbonyl, amino $C_1$–$C_6$ alkylcarbonyl, cinnamoyl, $C_1$–$C_6$ alkylcarbamoyl, di $C_1$–$C_6$ alkylsulfamoyl, $C_1$–$C_6$ alkylsulfonyl, di $C_1$–$C_6$ alkylaminothiocarbonyl, pyrimidyl and phenyl;

wherein the amino group in the amino $C_1$–$C_6$ alkylcarbonyl substituent may be substituted by $C_1$–$C_6$ alkoxycarbonyl;

wherein the cinnamoyl substituent may be substituted by $C_1$–$C_6$ alkoxy; and wherein the phenyl substituent may be substituted by halogen.

8. The compound according to claim 1, wherein r is 0, and $NR_{16}R_{17}$ is piperazinyl which may be substituted by a substituent selected from the group consisting of $C_1$–$C_6$ alkyl, $C_1$–$C_6$ alkylcarbonyl, $C_1$–$C_6$ alkoxycarbonyl, trihalo $C_1$–$C_6$ alkoxycarbonyl, $C_2$–$C_6$ alkenyloxycarbonyl, phenoxycarbonyl, benzyloxycarbonyl, amino $C_1$–$C_6$ alkylcarbonyl, cinnamoyl, $C_1$–$C_6$ alkylcarbamoyl, di $C_1$–$C_6$ alkylsulfamoyl, $C_1$–$C_6$ alkylsulfonyl, di $C_1$–$C_6$ alkylaminothiocarbonyl, pyrimidyl and phenyl;

wherein the amino group in the amino $C_1$–$C_6$ alkylcarbonyl substituent may be substituted by $C_1$–$C_6$ alkoxycarbonyl;

wherein the cinnamoyl substituent may be substituted by $C_1$–$C_6$ alkoxy; and wherein the phenyl substituent may be substituted by halogen.

* * * * *